(12) United States Patent
Iwadate et al.

(10) Patent No.: US 8,290,566 B2
(45) Date of Patent: Oct. 16, 2012

(54) MAGNETIC RESONANCE IMAGING APPARATUS AND IMAGE GENERATING METHOD

(75) Inventors: Yuji Iwadate, Tokyo (JP); Kenichi Kanda, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 369 days.

(21) Appl. No.: 12/420,974

(22) Filed: Apr. 9, 2009

(65) Prior Publication Data

US 2009/0259120 A1   Oct. 15, 2009

(30) Foreign Application Priority Data

Apr. 11, 2008   (JP) ................................. 2008-103549

(51) Int. Cl.
*A61B 5/05* (2006.01)
(52) U.S. Cl. .................... 600/410; 600/420; 324/318
(58) Field of Classification Search .................. 600/407, 600/410, 425, 444, 445; 324/309, 313, 318, 324/319
See application file for complete search history.

(56) References Cited

U.S. PATENT DOCUMENTS

| | | | |
|---|---|---|---|
| 5,000,182 A | 3/1991 | Hinks | |
| 5,251,128 A | 10/1993 | Crawford | |
| 5,287,276 A | 2/1994 | Crawford et al. | |
| 5,382,902 A | 1/1995 | Taniguchi et al. | |
| 5,420,510 A | 5/1995 | Fairbanks et al. | |
| 5,499,629 A * | 3/1996 | Kerr et al. | 600/410 |
| 5,779,636 A * | 7/1998 | Kanazawa | 600/410 |
| 6,073,041 A | 6/2000 | Hu et al. | |
| 6,144,201 A * | 11/2000 | Miyazaki | 324/306 |
| 6,201,393 B1 | 3/2001 | Bernstein et al. | |
| 6,275,720 B1 | 8/2001 | Du et al. | |
| 6,486,668 B1 * | 11/2002 | Ma | 324/307 |
| 6,489,766 B1 * | 12/2002 | Alsop | 324/313 |
| 6,535,754 B2 | 3/2003 | Fishbein et al. | |
| 6,690,963 B2 | 2/2004 | Ben-Haim et al. | |

(Continued)

FOREIGN PATENT DOCUMENTS

JP   10-277010   10/1998

(Continued)

OTHER PUBLICATIONS

Yiping P. Du, Manojkumar Saranathan, and Thomas K. F. Foo. "An Accurate, Robust, and Computationally Efficient Navigator Algorithm for Measuring Diaphragm Positions", Journal of Cardiovascular Magnetic Resonance vol. 6, No. 2, pp. 483-490, 2004.

(Continued)

*Primary Examiner* — James Kish
*Assistant Examiner* — Michael N Fisher
(74) *Attorney, Agent, or Firm* — Armstrong Teasdale LLP

(57) ABSTRACT

A magnetic resonance imaging apparatus includes a first navigator data processor that generates a first phase profile based on first navigator data acquired by executing a first navigator sequence, generates a position profile indicative of a relationship between a plurality of region positions and time at which the first navigator sequence is executed, and detects a specific position in the position profile. A second navigator data processor generates a second phase profile based on second navigator data acquired by executing a second navigator sequence, detects the position of each region with respect to each second phase profile within a reference range set so as to contain the specific position, based on each second phase profile, and acquires the same as its corresponding position data.

20 Claims, 14 Drawing Sheets

U.S. PATENT DOCUMENTS

| | | |
|---|---|---|
| 6,771,997 B2 | 8/2004 | Schaffer |
| 6,885,193 B2 | 4/2005 | Foxall |
| 6,894,494 B2 | 5/2005 | Stergiopoulos et al. |
| 7,012,603 B2 | 3/2006 | Chen et al. |
| 7,174,200 B2 | 2/2007 | Salerno et al. |
| 7,332,911 B2 | 2/2008 | Iwadate et al. |
| 7,432,710 B2 | 10/2008 | Takei et al. |
| 2004/0092809 A1 | 5/2004 | DeCharms |
| 2004/0147832 A1 | 7/2004 | Fishbein et al. |
| 2006/0224062 A1 | 10/2006 | Aggarwal et al. |
| 2007/0080690 A1* | 4/2007 | Takei et al. .................. 324/318 |
| 2007/0088212 A1 | 4/2007 | Takei et al. |
| 2007/0255130 A1* | 11/2007 | Du .............................. 600/410 |
| 2009/0259120 A1* | 10/2009 | Iwadate et al. ............... 600/410 |
| 2009/0270720 A1 | 10/2009 | Iwadate et al. |

FOREIGN PATENT DOCUMENTS

| | | |
|---|---|---|
| JP | 2007-098026 | 4/2007 |
| JP | 2007-111188 | 5/2007 |

OTHER PUBLICATIONS

Non-Final Office Action for U.S. Appl. No. 11/538,878 mailed Jan. 9, 2008; 8 pages.

Non-Final Office Action for U.S. Appl. No. 12/429,033 mailed Aug. 29, 2011; 14 pages.

\* cited by examiner

MAGNETIC RESONANCE IMAGING APPARATUS AND IMAGE GENERATING METHOD

CROSS REFERENCE TO RELATED APPLICATIONS

This application claims the benefit of Japanese Patent Application No. 2008-103549 filed Apr. 11, 2008, which is hereby incorporated by reference in its entirety.

BACKGROUND OF THE INVENTION

The embodiments described herein relate to a magnetic resonance imaging apparatus (MRI) and an image generating method, and particularly to a magnetic resonance imaging apparatus which executes scans for transmitting RF pulses to a subject within a static magnetic field space and collecting or acquiring magnetic resonance signals from the subject thereby to generate an image of the subject, and an image generating method for detecting the position of each region in a subject, which is obtained by executing each scan and thereby generating an image.

A magnetic resonance imaging apparatus executes scans for applying an electromagnetic wave to a subject lying within a static magnetic field space thereby to excite spins of proton in the subject by a nuclear magnetic resonance phenomenon and acquiring magnetic resonance signals generated by the excited spins. This is of an apparatus that generates a slice image with respect to a tomographic plane of the subject, based on the magnetic resonance signals obtained by the scans.

There is a case in which body-motion artifacts occur in the generated slice image where body motion occurs in the subject upon imaging the subject using the magnetic resonance imaging apparatus. When, for example, the heart or abdominal region of the subject is imaged or photographed, body motion artifacts occur due to body motion such as breathing exercises, cardiac motion or the like, thus degrading the quality of the image.

Thus, there have been proposed methods for solving the problem of the degradation in the image due to the body motion artifacts. One method thereof is that upon imaging or photography under normal respiration, for example, an excitation section of a subject is corrected in real time according to a change in the position of a diaphragm and each magnetic resonance signal is always measured from the same section, thereby preventing the degradation in the image due to the body motion artifacts. An imaging sequence is changed or imaging data is selected through the use of acquired navigator echoes, thereby preventing degradation in image quality due to body motion artifacts (refer to, for example, Japanese Unexamined Patent Publication No. 2007-111188 and Japanese Unexamined Patent Publication No. 2007-98026).

As an approach for detecting the position of the diaphragm, which is used in these techniques, there has been known a method for tracking or scanning the motion of the diaphragm using navigator echoes and performing respiratory synchronization and gating using acquired navigator data (refer to, for example, Japanese Unexamined Patent Publication No. Hei 10(1998)-277010).

For example, a signal intensity profile obtained by plotting the relationship between a signal intensity I of navigator data and the position X in a navigator area is generated. In the generated signal intensity profile, for example, the position of the diaphragm lying in the boundary between the liver and lung is calculated and respiratory synchronization is performed.

As a method for calculating the position of the diaphragm in the signal intensity profile, there has been known, for example, a differential method or a Du method or the like (refer to, for example, JOURNAL OF CARDIOVASCULAR MAGNETIC RESONANCE, Vol. 6, No. 2, pp. 483-490, 2004).

However, as a result that as shown in a coronal image of FIG. 15, an imaging area IA for executing an imaging scan to acquire imaging data has overlapped with a navigator area NA corresponding to the position of acquisition of navigator data, signal disturbance due to slice interference occurs in the acquired navigator data. As indicated by a broken-line area of FIG. 16, a low-signal region occurs in a signal intensity profile. Here, the broken-line area shown in FIG. 16 indicates a signal intensity profile corresponding to a portion where the imaging area IA and the navigator area NA shown in FIG. 15 overlap. In doing so, it became difficult to obtain a stable analytic result by the conventional navigator data analyzing method shown above.

Thus, there has been considered a method for suppressing the occurrence of signal disturbance due to the interference of an imaging scan by using phase information of navigator data.

However, though the occurrence of the signal disturbance due to the interference of the imaging scan can be suppressed by using the phase information of the navigator data, a problem arises in that since variations are apt to occur in the phase at a region low in signal intensity, it is difficult to obtain the result of analysis of navigator data stably, thus causing degradation in image quality.

It is desirable that the problem described previously is solved.

BRIEF DESCRIPTION OF THE INVENTION

In one aspect, a magnetic resonance imaging apparatus is provided that repeatedly executes a first navigator sequence for acquiring magnetic resonance signals from a navigator area containing body-moved regions of a subject as first navigator data and repeatedly executes a second navigator sequence for acquiring magnetic resonance signals from the navigator area as second navigator data and an imaging sequence for acquiring magnetic resonance signals from an imaging area at the subject as imaging data, based on the positions of the regions obtained from the second navigator data, based on the first navigator data, thereby acquiring the imaging data as raw data, and thereafter generates an image, based on the raw data, comprising a first navigator data processor for generating a phase profile for each of the first navigator data as a first phase profile with respect to each of the first navigator data, detecting a position of each region with respect to each first phase profile, generating a position profile indicative of a relationship between a plurality of the region positions and time at which the first navigator sequence is repeatedly executed, and detecting a specific position in the position profile; a second navigator data processor for generating a phase profile for each of the second navigator data as a second phase profile with respect to each of the second navigator data, detecting the position of each region with respect to each second phase profile within a reference range set so as to contain the specific position, based on each second phase profile, and acquiring the same as its corresponding position data; and a raw data acquiring unit for acquiring as raw data, imaging data obtained by the imaging sequence corresponding to the second navigator sequence, based on the position data.

Preferably, the first navigator data processor includes an intensity profile generation device for generating an intensity profile indicative of a relationship between the intensity of each of the first navigator data and each position in the navigator area with respect to each of the first navigator data, a first position detection device for detecting the position of each region with respect to each intensity profile and acquiring the same as its corresponding first position data, a first reference range set device for setting a first reference range with respect to each intensity profile in such a manner that the first reference range contains data corresponding to the first position data, a first phase profile generation device for generating a first phase profile indicative of a relationship between the phase of each first navigator data and each position in the navigator area with respect to each of the first navigator data, a second position detection device for detecting the position of the region within each first reference range with respect to each first phase profile and acquiring the same as its corresponding second position data, a first position profile generation device for generating a first position profile indicative of a relationship between respective positions corresponding to the respective second position data and time at which the first navigator sequence is repeatedly executed, and a specific position detection device for detecting a specific position in the first position profile. The second navigator data processor includes a second phase profile generation device for generating a second phase profile indicative of a relationship between the phase of each second navigator data and each position in the navigator area with respect to each second navigator data, a second reference range set device for setting a second reference range in such a manner that the second reference range contains the specific position at each region, which has been detected by the specific position detection device, a third position detection device for detecting the position of each region with respect to each second phase profile within the second reference range and acquiring the same as its corresponding third position data, and a second position profile generation device for generating a second position profile indicative of a relationship between the positions corresponding to the respective third position data and time at which the second navigator sequence is repeatedly executed.

Preferably, the raw data acquisition device selects as raw data, imaging data acquired during the time corresponding to the second position data lying within a third reference range set so as to contain the specific position of each region, from the imaging data.

Preferably, when the second position data fall within the third reference range set so as to contain the specific position of each region, an imaging sequence is executed to acquire imaging data.

Preferably, the specific position detection device detects an area largest in the number of position data, which is contained in respective areas obtained by dividing the position in the first position profile in predetermined width, as the specific position of each region.

Preferably, the specific position detection device detects a minimum value of the position data in the first position profile as the specific position of each region.

Preferably, each of the first navigator data and the second navigator data is obtained from a diaphragm as the region.

Preferably, the intensity profile generation device one-dimensionally Fourier transforms the first navigator data thereby to generate the intensity profile, the first phase profile generation device one-dimensionally Fourier transforms the first navigator data thereby to generate the first phase profile, and the second phase profile generation device one-dimensionally Fourier transforms the second navigator data thereby to generate the second phase profile.

Preferably, the first position detection device obtains the first position data by a differential method.

Preferably, the second position detection device obtains the second position data by the differential method.

Another aspect provides an image generating method which repeatedly executes a first navigator sequence for acquiring magnetic resonance signals from a navigator area containing body-moved regions of a subject as first navigator data and repeatedly executes a second navigator sequence for acquiring magnetic resonance signals from the navigator area as second navigator data and an imaging sequence for acquiring magnetic resonance signals from an imaging area at the subject as imaging data, based on the positions of the regions obtained from the second navigator data, based on the first navigator data, thereby acquiring the imaging data as raw data, and thereafter generates an image, based on the raw data, including the steps: a first step for generating a phase profile for each of the first navigator data as a first phase profile with respect to each of the first navigator data, detecting a position of each region with respect to each first phase profile, generating a position profile indicative of a relationship between a plurality of the region positions and time at which the first navigator sequence is repeatedly executed, and detecting a specific position in the position profile; a second step for generating a phase profile for each of the second navigator data as a second phase profile with respect to each of the second navigator data, detecting the position of each region with respect to each second phase profile within a reference range set so as to contain the specific position, based on each second phase profile, and acquiring the same as its corresponding position data; and a third step for acquiring the imaging data as raw data, based on the position data obtained in the second step.

Preferably, the first step includes a fourth step for generating an intensity profile indicative of a relationship between the intensity of each of the first navigator data and each position in the navigator area, a fifth step for detecting the position of each region with respect to the intensity profile generated in the fourth step and acquiring the same as first position data, a sixth step for setting a first reference range with respect to the intensity profile in such a manner that the first reference range contains data corresponding to the first position data obtained in the fifth step, a seventh step for generating a first phase profile indicative of a relationship between the phase of the first navigator data and each position in the navigator area, an eighth step for detecting the position of each region within the first reference range set in the sixth step with respect to the first phase profile generated in the seventh step and acquiring the same as second position data, a ninth step for generating a first position profile indicative of a relationship between a plurality of the second position data obtained by repeatedly executing the fourth through eighth steps and time at which the first navigator sequence is repeatedly executed, and a tenth step for detecting a specific position in the first position profile generated in the ninth step, and the second step includes an eleventh step for generating a second phase profile indicative of a relationship between the phase of the second navigator data and each position in the navigator area, a twelfth step for setting a second reference range in such a manner that the second reference range contains the specific position at each region, which has been detected in the tenth step, a thirteenth step for detecting the position of each region with respect to the second phase profile generated in the eleventh step within the second reference range set in the twelfth step and acquiring the same as third position data, and a fourteenth step for generating a second position profile indicative of a relationship between a plurality of the third position data obtained by repeatedly executing the eleventh through thirteenth steps and time at which the second navigator sequence is repeatedly executed.

Preferably, the third step includes a step for setting a third reference range from the imaging data in such a manner that the third reference range contains the specific position of each region, and a step for selecting, as raw data, imaging data acquired during the time corresponding to the second position data lying within the third reference range.

Preferably, the third step includes a step for setting the third reference range from the imaging data in such a manner that the third reference range contains the specific position of each region, and when the second position data fall within the third reference range, an imaging sequence is executed to acquire imaging data.

Preferably, in the tenth step, an area largest in the number of data at each position in the first position profile, which is contained in respective areas obtained by dividing the position in the first position profile in predetermined width, is detected as the specific position of each region.

Preferably, in the tenth step, a minimum value of each position in the first position profile is detected as the specific position of each region.

Preferably, each of the first navigator data and the second navigator data is obtained from a diaphragm as the region.

Preferably, in the fourth step, the second navigator data is one-dimensionally Fourier transformed thereby to generate the intensity profile in the fourth step, the first navigator data is one-dimensionally Fourier transformed thereby to generate the first phase profile in the sixth step, and the second navigator data is one-dimensionally Fourier transformed thereby to generate the second phase profile in the ninth step.

Preferably, in the fifth step, the first position data is detected by a differential method.

Preferably, in the seventh step, the second position data is detected by the differential method.

According to the embodiments described herein a magnetic resonance imaging apparatus is provided that is capable of enhancing image quality by obtaining a stable result of analysis of navigator data, and an image generating method capable of improving image quality.

Further objects and advantages of the embodiments described herein will be apparent from the following description as illustrated in the accompanying drawings.

DETAILED DESCRIPTION OF THE INVENTION

Figure 1:
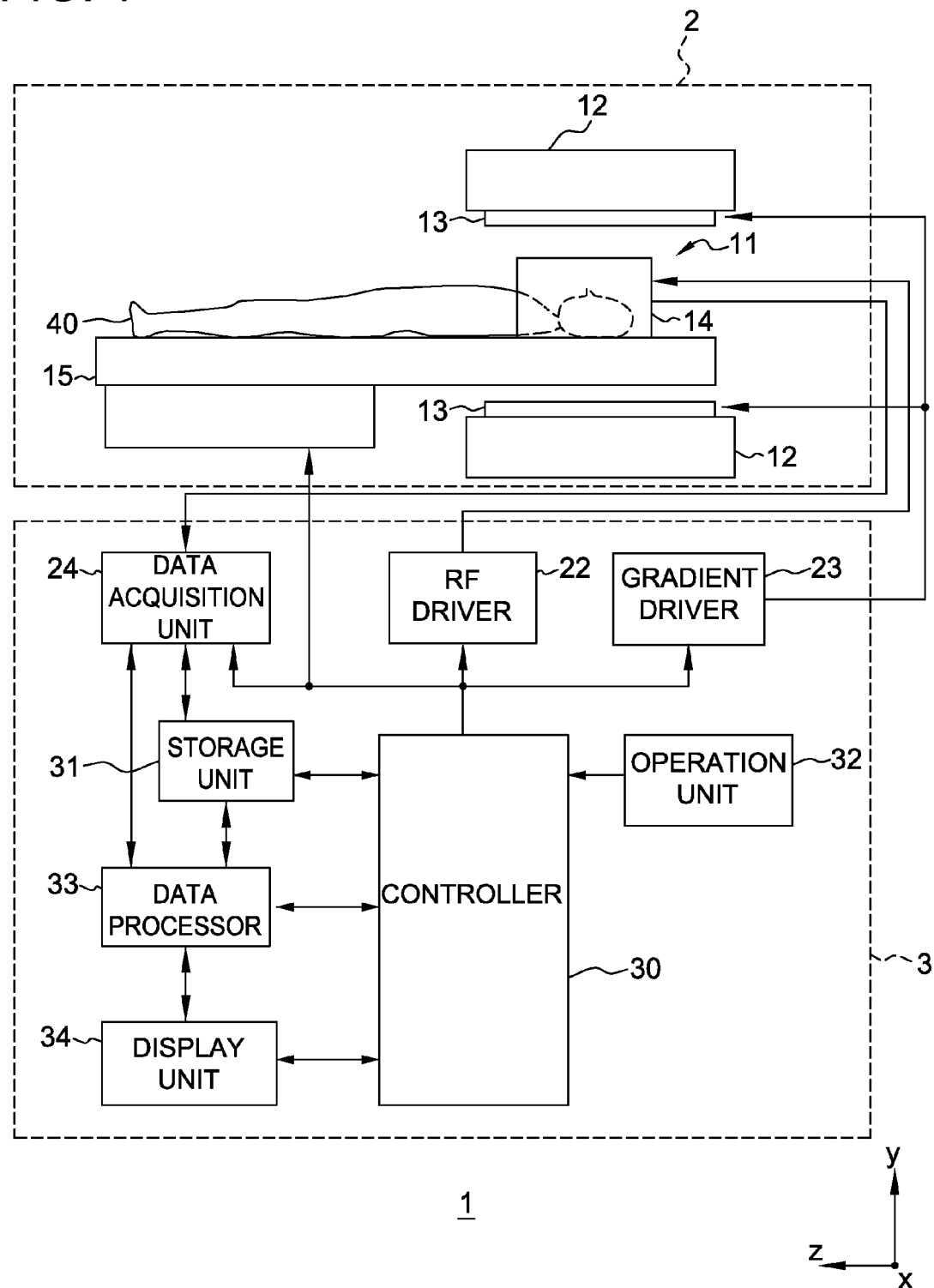
FIG. 1 is a constructional diagram showing a construction of an exemplary magnetic resonance imaging apparatus constructed by an RF coil unit.

FIG. 1 is a constructional diagram showing a construction of an exemplary magnetic resonance imaging apparatus configured by an RF coil unit.

As shown in FIG. 1, the magnetic resonance imaging apparatus 1 has a scan section 2 and an operation console section 3. Here, the scan section 2 has a static magnetic field magnet unit 12, a gradient coil unit 13, an RF coil unit 14 and a cradle 15. The operation console section 3 has an RF driver 22, a gradient driver 23, a data acquisition unit 24, a controller 30, a storage unit 31, an operation unit 32, a data processor 33 and a display unit 34.

The scan section 2 will be explained.

As shown in FIG. 1, the scan section 2 includes a static magnetic field space 11 in which an imaging slice area in a subject 40 is held or accommodated. The scan section 2 applies RF pulses to the corresponding imaging area of the subject 40 held in the static magnetic filed space 11 formed with a static magnetic field, based on a control signal outputted from the operation console unit 3 and executes a scan for acquiring each magnetic resonance signal from the imaging area thereof.

In the present embodiment, the scan section 2 repeatedly executes a navigator sequence NS for acquiring a magnetic resonance signal generated at a navigator area NA of the subject 40 as navigator data a prescan. Upon an actual scan, the scan section 2 repeatedly executes an imaging sequence IS for obtaining a magnetic resonance signal generated at an imaging area IA of the subject 40 as imaging data, and a navigator sequence NS for acquiring a magnetic resonance signal generated at a navigator area NA of the subject 40 as navigator data.

Respective constituent elements of the scan section 2 will be explained sequentially.

The static magnetic field magnet unit 12 is provided to form a static magnetic field in the static magnetic field space 11 with the subjected 40 held therein. The static magnetic field magnet unit 12 is of a horizontal magnetic field type and forms a static magnetic field through a superconductive magnet (not shown) so as to extend along a body-axis direction (z direction) of the subject 40 placed in the static magnetic field space 11 with the subject 40 accommodated therein. Incidentally, the static magnetic field magnet unit 12 may be of a vertical magnetic field type in addition to the horizontal magnetic field type. Alternatively, the static magnetic field magnet unit 12 may be constituted of a permanent magnet.

The gradient coil unit 13 forms a gradient magnetic field in the static magnetic field space 11 to cause each magnetic resonance signal received by the RF coil unit 14 to have three-dimensional position information. The gradient coil unit 13 has gradient coils of three systems to form three types of gradient magnetic fields corresponding to a slice selection gradient magnetic field, a read gradient magnetic field and a phase encode gradient magnetic field.

The RF coil unit 14 is disposed so as to surround the subject 40, for example. The RF coil unit 14 transmits each RF pulse corresponding to an electromagnetic wave to the subject 40, based on a control signal supplied from the controller 30 within the static magnetic field space 11 formed with the static magnetic field by the static magnetic field magnet unit 12 thereby to form a high frequency magnetic field. Consequently, the spins of proton in the imaging slice area of the subject 40 are excited. The RF coil unit 14 receives an electromagnetic wave generated when each of the excited spins of proton in the imaging slice area of the subject 40 is returned to its original magnetization vector, as a magnetic resonance signal. The RF coil unit 14 may perform the transmission/reception of each RF pulse through the same RF coil.

In the present embodiment, the RF coil unit 14 transmits RF pulses in the navigator sequence NS and the imaging sequence IS.

The cradle 15 has a table that places the subject 40 thereon. The cradle 15 moves the subject 40 placed on the table between the inside and outside of the static magnetic field space 11, based on a control signal supplied from the controller 30.

The operation console section 3 will be explained.

The operation console section 3 controls the scan section 2 in such a manner that the scan section 2 executes scans for the subject 40. The operation console section 3 generates an image of the subject 40, based on magnetic resonance signals obtained by the scans executed by the scan section 2 and displays the generated image.

Respective parts that constitute the operation console section 3 will be described sequentially.

The RF driver 22 has a gate modulator (not shown), an RF power amplifier (not shown) and an RF oscillator (not shown) to form a high frequency magnetic field within the static magnetic field space 11 by driving the RF coil unit 14. The RF driver 22 modulates an RF signal sent from the RF oscillator to a signal having predetermined timing and predetermined envelope using the gate modulator on the basis of the control signal outputted from the controller 30. The RF signal modulated by the gate modulator is amplified by the RF power amplifier, followed by being outputted to the RF coil unit 14.

The gradient driver 23 drives the gradient coil unit 13 based on the control signal of the controller 30 to generate a gradient magnetic field within the static magnetic field space 11. The gradient driver 23 has three-system drive circuits (not shown) in association with the three-system gradient coils of the gradient coil unit 13.

The data acquisition unit 24 has a phase detector (not shown) and an analog/digital converter (not shown) to collect or acquire the magnetic resonance signals received by the RF coil unit 14. The data acquisition unit 24 phase-detects each magnetic resonance signal sent from the RF coil unit 14 by the phase detector with the output of the RF oscillator of the RF driver 22 as a reference signal, and outputs the phase-detected signal to the analog/digital converter. Then, the data acquisition unit 24 converts the magnetic resonance signal corresponding to the analog signal phase-detected by the phase detector into a digital signal by means of the analog/digital converter and outputs it therefrom.

In the present embodiment, the data acquisition unit 24 outputs a magnetic resonance signal obtained as imaging data by the imaging sequence executed by the scan section 2 and a magnetic resonance signal obtained as navigator data by the navigator sequence to the storage unit 31 and data processor 33 to be described later.

The controller 30 has a computer and a program that allows each part to execute an operation corresponding to a predetermined scan using the computer. The controller 30 is connected to the operation unit 32 to be described later. The controller 30 processes an operation signal inputted to the operation unit 32 and outputs a control signal to the respective parts of the cradle 15, RF driver 22, gradient driver 23 and data acquisition unit 24 to control them. In order to acquire a desired image, the controller 30 controls the data processor 33 and the display unit 34, based on the operation signal sent from the operation unit 32.

In the present embodiment, the controller 30 controls the RF driver 22 and the gradient driver 23 to allow the scan section 2 to execute the navigator sequence NS and the imaging sequence IS. The controller 30 executes control of the imaging sequence IS executed by the scan section 2, based on the navigator data obtained by executing the navigator sequence NS.

The storage unit 31 has a computer and a program for causing the computer to execute predetermined data processing. The storage unit 31 stores therein navigator data prior to data processing acquired by the data acquisition unit 24, imaging data corresponding to each magnetic resonance signal prior to image generation processing, navigator data data-processed by the data processor 33 to be described later, and image data or the like subjected to the image generation processing.

The operation unit 32 is made up of operation devices such as a keyboard, a mouse and the like. The operation unit 32 inputs operation data, an imaging protocol and the like therein through an operator. Further, the operation unit 32 sets an area for executing the imaging sequence IS and an area for executing the navigator sequence NS and outputs the operation data, the imaging protocol and data related to each setting area to the controller 30.

The data processor 33 has a computer and a memory that stores a program that executes predetermined data processing using the computer. The data processor 33 performs data processing, based on the corresponding control signal sent from the controller 30.

Figure 2:
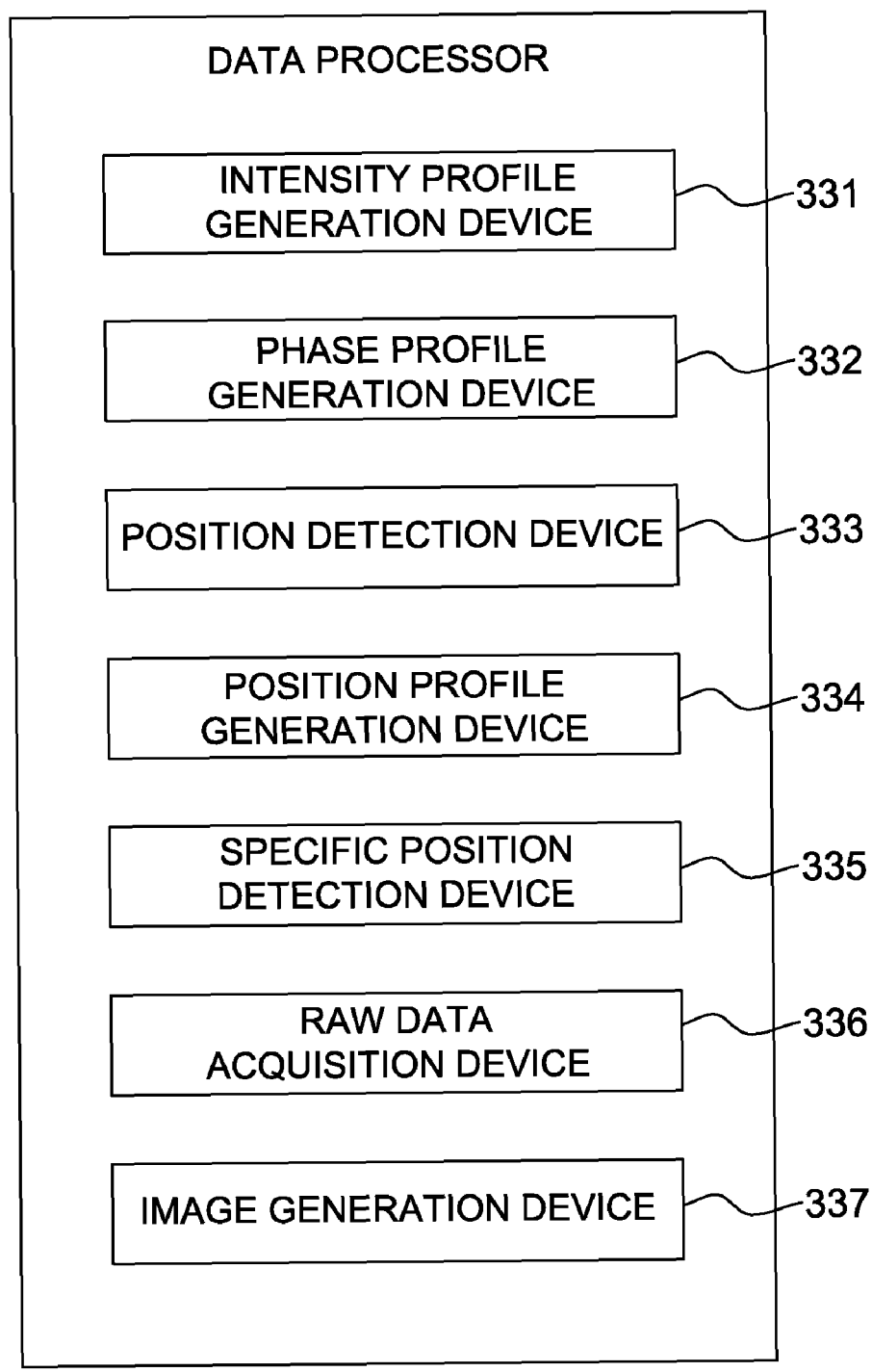
FIG. 2 is a block diagram illustrating a construction of a data processor that may be used with the magnetic resonance imaging apparatus shown in FIG. 1.

Here, FIG. 2 is a block diagram showing a construction of the data processor 33.

As shown in FIG. 2, the data processor 33 has an intensity profile generation device 331, a phase profile generation device 332, a position detection device 333, a position profile generation device 334, a specific position detection device 335, a raw data acquisition device 336 and an image generation device 337.

The respective parts of the data processor 33 will be explained sequentially.

The intensity profile generation device 331 has a computer and a memory that stores a program that causes the computer to execute predetermined data processing. Upon the prescan, the intensity profile generation device 331 generates a plurality of intensity profiles about a navigator area NA of a subject 40 by using as raw data, magnetic resonance signals obtained as navigator data by executing the navigator sequence NS about the navigator area NA of the subject 40 plural times.

Upon the actual scan, the intensity profile generation device 331 generates intensity profiles about a navigator area NA of a subject 40 by using as raw data, magnetic resonance signals obtained as navigator data by a navigator sequence NS executed before execution of an imaging sequence IS about an imaging area IA of the subject 40, for example.

That is, in the present embodiment, upon execution of the navigator sequence NS by the scan section 2 plural times, the intensity profile generation device 331 generates a plurality of intensity profiles by subjecting to one-dimensional Fourier transform, navigator data collected into the data acquisition unit 24 by allowing the RF coil unit 14 to transmit RF pulses to the navigator area NA and allowing the RF coil unit 14 to receive magnetic resonance signals generated in an imaging area thereof and plotting the relationship between the intensity m and position X of the one-dimensionally Fourier-transformed data.

The phase profile generation device 332 has a computer and a memory that stores a program for allowing the computer to execute predetermined data processing. Upon the prescan, the phase profile generation device 332 generates a plurality of phase profiles with respect to a navigator area NA of a subject 40 by using as raw data, magnetic resonance signals obtained as navigator data by executing the navigate sequence NS about the navigator area NA of the subject 40 plural times.

Upon the actual scan, the phase profile generation device 332 generates phase profiles about a navigator area NA of a subject 40 by using as raw data, magnetic resonance signals obtained as navigator data by a navigator sequence NS executed before the execution of an imaging sequence IS about an imaging area IA of the subject 40, for example.

That is, in the present embodiment, upon execution of the navigator sequence NS by the scan section 2 plural times, the phase profile generation device 332 generates a plurality of phase profiles by subjecting to one-dimensional Fourier transform, navigator data collected into the data acquisition unit 24 by allowing the RF coil unit 14 to transmit RF pulses to the navigator area NA and allowing the RF coil unit 14 to receive magnetic resonance signals generated in an imaging area thereof and plotting the relationship between the phase P and position Xp of the one-dimensionally Fourier-transformed data.

The position detection device 333 has a computer and a memory that stores a program that causes the computer to execute predetermined data processing. The position detection device 333 detects the position of each region in the subject 40, based on a control signal sent from the controller 30. In the present embodiment, the position detection device 333 detects a position Xm of each region in the subject 40 at each of the plural intensity profiles generated based on the navigator data subjected to one dimensional Fourier transform by the intensity profile generation device 331. As a method for detecting the same, may be mentioned, for example, a differential method, a Du method or the like. As the position Xm of the region in the subject 40, for example, a position Xmd of a diaphragm 62 lying in the boundary between a lung 60 and a liver 61 in the subject 40 is detected.

The position detection device 333 detects a position Xp of each region in the subject 40 at each of the plural phase profiles generated based on the navigator data subjected to one dimensional Fourier transform by the phase profile generation device 332. As its detecting method, may be mentioned, for example, the differential method, the Du method or the like. As the position Xp of the region in the subject 40, for example, a position Xpd of the diaphragm 62 lying in the boundary between the lung 60 and the liver 61 in the subject 40 is detected.

The position profile generation device 334 has a computer and a memory that stores a program that causes the computer to execute predetermined data processing. The position profile generation device 334 generates a position profile indicative of the relationship between positions Xp of each region in the subject 40, which have been detected for every predetermined time, and time.

In the present embodiment, the position profile generation device 334 generates a position profile by plotting the relationship between the position Xp of each region, which has been detected by the position detection device 333, and time t. As a method for detecting the same, may be mentioned, for example, the differential method, the Du method or the like. As the position Xp of the region in the subject 40, for example, a position Xpd of the diaphragm 62 lying in the boundary between the lung 60 and the liver 61 in the subject 40 is detected.

The specific position detection device 335 has a computer and a memory that stores a program that causes the computer to execute predetermined data processing. The specific position detection device 335 detects a specific position of each region in the subject 40, based on the control signal supplied from the controller 30. In the present embodiment, the specific position detection device 335 detects a specific position of each region in the subject 40 at each position profile generated by the position profile generation device 334. As the specific position, for example, a position Xpde of the diaphragm 62 lying in the boundary between the lung 60 and liver 61 at the time that the expiration of the subject 40 has been completed, is detected. As the specific position as well, the position of the diaphragm 62 lying in the boundary between the lung 60 and liver 61 at the time that inspiration has been made, may be detected.

As a method for detecting the position of the diaphragm 62 at the time that the expiration has been ended, for example, the position in the position profile is divided in predetermined width and the area largest in the number of positional data, of the so-divided respective areas is detected as the position Xpde of the diaphragm 62 at the time that the expiration has been completed.

The minimum value of the position Xtd of the diaphragm 62 in the position profile is detected as the position Xpde of the diaphragm 62 at the time that the expiration has been ended.

An allowable range AW is set so as to contain the detected position Xpde of the diaphragm 62 at the time that the expiration has been completed. The allowable range AW is set as ±2 mm as viewed from the detected position Xpde of the diaphragm 62 at the time that the expiration has been ended.

The raw data acquisition device 336 has a computer and a memory that stores a program that causes the computer to execute predetermined data processing. The raw data acquisition device 336 executes data processing for acquiring imaging data obtained by allowing the scan section 2 to carry out the imaging sequence IS as raw data, based on the corresponding position profile generated by the position profile generation device 334.

Here, the raw data acquisition device 336 determines whether the position profile generated by the position profile generation device 334 falls within the allowable range AW set in advance, and acquires imaging data corresponding to navigator data in which the position profile lying within the allowable range AW has been generated. When, for example, a navigator sequence NS is first performed and an imaging sequence IS is then performed to acquire navigator data and imaging data upon the actual scan, the imaging data obtained by the imaging sequence IS conducted subsequent to the navigator sequence is acquired as raw data.

The image generation device 337 has a computer and a memory that stores a program that causes the computer to execute predetermined data processing. The image generation device 337 generates an image about the imaging area of the subject 40 by using the raw data acquired by the raw data acquisition device 336. That is, in the present embodiment, the raw data acquisition device 336 acquires as raw data, imaging data collected or acquired by allowing the RF coil unit 14 to transmit RF pulses to the corresponding imaging area and allowing the RF coil unit 14 to receive magnetic resonance signals generated in the imaging area, based on the position profile upon execution of the imaging sequence IS by the scan section 2, and generates a slice image of the subject 40, based on the acquired raw data. The image generation device 337 outputs the generated slice image to the display unit 34.

The display unit 34 is made up of a display device such as a display or the like and displays an image on its display screen, based on the corresponding control signal sent from the controller 30. The display unit 34 displays, for example, an image about each input term for operation data inputted to the operation unit 32 by an operator on the display screen. The display unit 34 displays the slice image of the subject 40 generated by the image generation device 337.

In the present embodiment, there is a case in which the display unit 34 displays the intensity profile, phase profile or position profile.

The operation of imaging or photographing the subject 40 will be explained below using the magnetic resonance imaging apparatus 1 according to the present embodiment.

Figure 3:
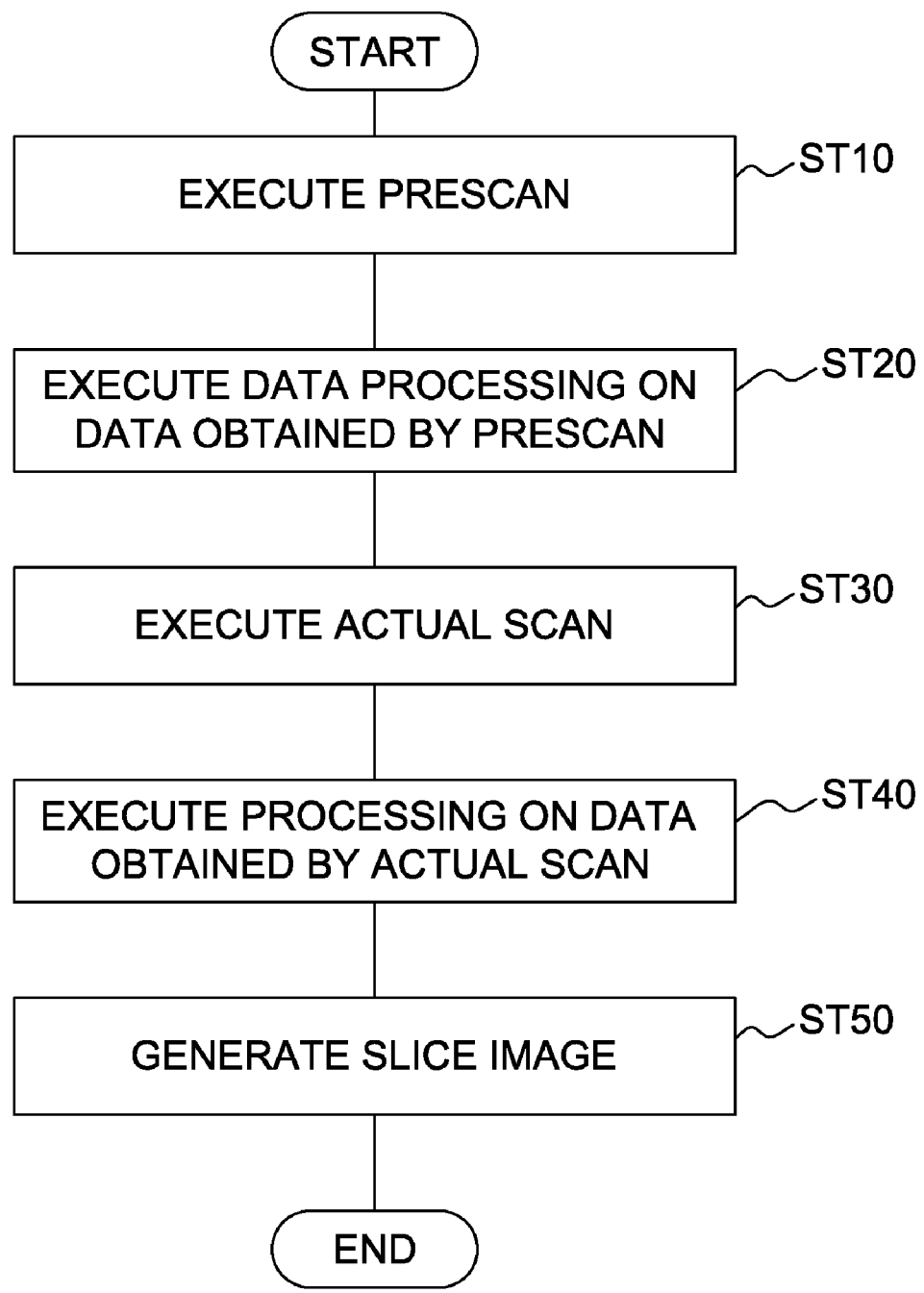
FIG. 3 is a flow chart showing the operation of imaging a subject using the magnetic resonance imaging apparatus shown in FIG. 1.
Figure 4:
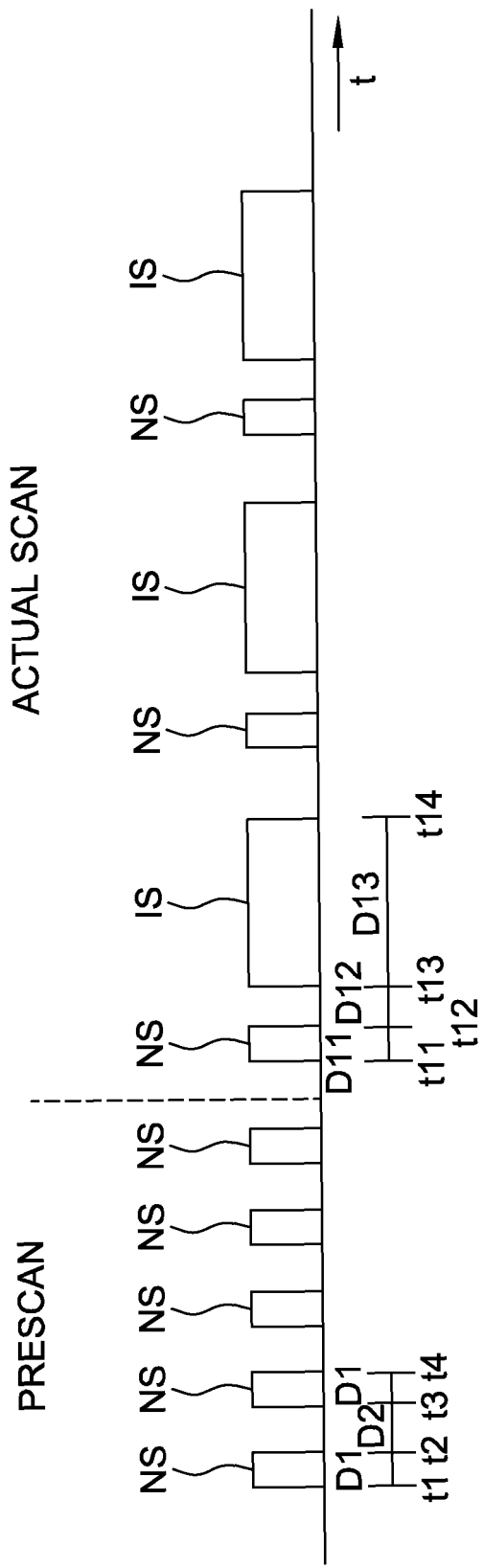
FIG. 4 is a sequence diagram illustrating a sequence used when the subject is scanned using the magnetic resonance imaging apparatus shown in FIG. 1.
Figure 5:
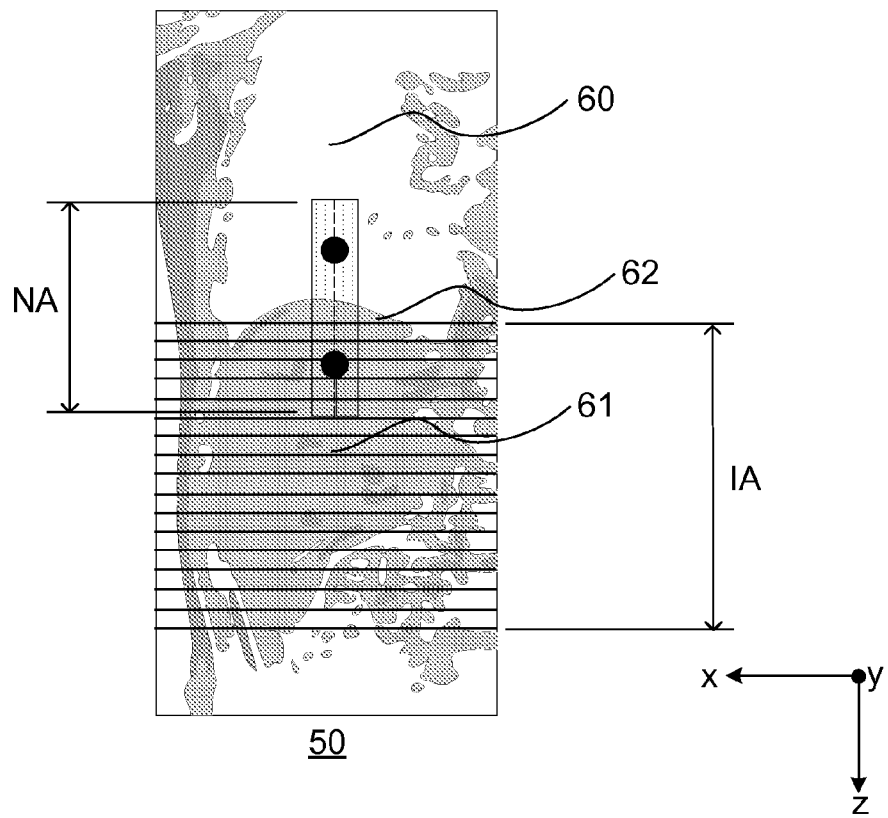
FIG. 5 is a diagram depicting a coronal image indicating a navigator area NA and an imaging area IA.
Figure 6:
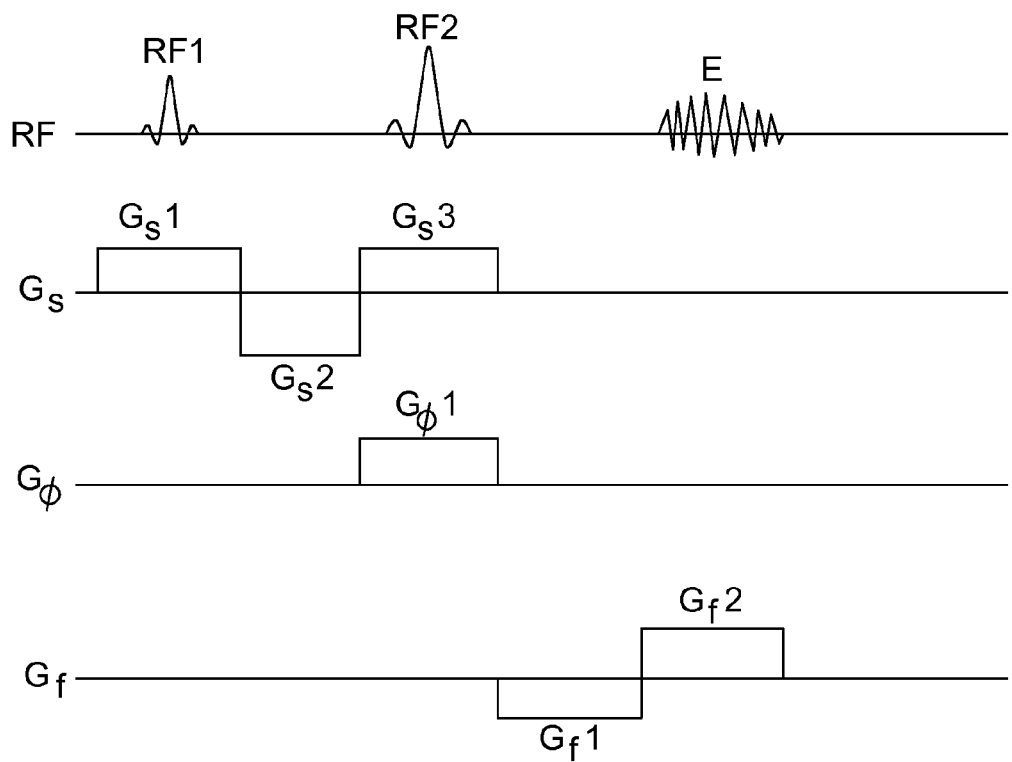
FIG. 6 is a diagram showing a pulse sequence indicative of a navigator sequence that may be used with the magnetic resonance imaging apparatus shown in FIG. 1.
Figure 7:
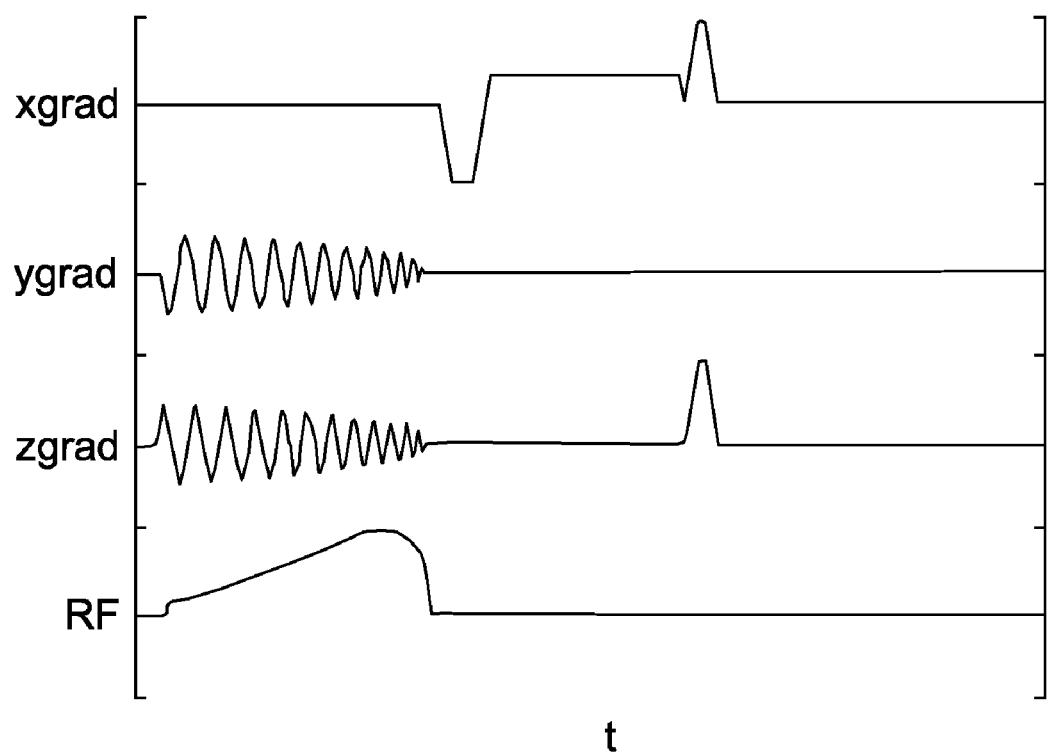
FIG. 7 is a diagram illustrating a pulse sequence indicative of a cylindrical navigator sequence that may be used with the magnetic resonance imaging apparatus shown in FIG. 1.

FIG. 3 is a flow chart showing the operation of imaging a subject in the one embodiment according to the invention. FIG. 4 is a sequence diagram showing a sequence used when the subject 40 is scanned in the one embodiment according to the invention. The horizontal axis indicates a time base t. FIG. 5 is a diagram depicting a coronal image indicating a navigator area NA and an imaging area IA in the one embodiment according to the invention. A z direction shown in FIG. 5 indicates the direction of a position X on the horizontal axis in FIGS. 9(a) and 9(b) to be described later. Incidentally, a black area indicates a lung 60 here. A gray area indicates a liver 61 and a diaphragm 62 is located between the lung 60 and the liver 61. A rectangular area whose long side is located in a z-axis direction approximately orthogonal to the diaphragm 62 indicates a navigator area NA for executing a navigator sequence NS. At the liver 61 in the coronal image, an area located so as to be parallel to an x-axis direction approximately parallel to the diaphragm 62 indicates an imaging area IA for executing an imaging sequence IS. FIG. 6 is a diagram showing a pulse sequence indicative of a navigator sequence in the one embodiment according to the invention. $G_s$ indicates a slice selection gradient magnetic field, $G_\varphi$ indicates a phase encoding gradient magnetic field, $G_f$ indicates a frequency encoding gradient magnetic field, and RF indicates a high frequency pulse, respectively. Incidentally, the vertical axis indicates intensity and the horizontal axis indicates time respectively here. FIG. 7 is a diagram showing a pulse sequence corresponding to a cylindrical gradient echo-type navigator sequence in the one embodiment according to the invention. RF indicates a high frequency pulse. In this figure, xgrad indicates a gradient magnetic field applied in an x-axis direction, ygrad indicates a gradient magnetic field applied in a y-axis direction, zgrad indicates a gradient magnetic field applied in a z-axis direction, and RF indicates a high frequency pulse. Incidentally, the vertical axis indicates intensity and the horizontal axis indicates time, respectively here.

As shown in FIG. 3, the prescan is first executed (ST10).

Here, the scan section 2 repeatedly executes a navigator sequence NS for the subject 40 to acquire navigator data used when the position X of each region in the subject 40 is detected.

For example, the scan section 2 repeatedly executes the navigator sequence NS as the prescan as shown in FIG. 4. The navigator sequence NS is executed between a time t1 at which the navigator sequence NS is started and a time t2 at which a predetermined time D1 has elapsed. Then, the navigator sequence NS is conducted between a time t3 at which a predetermined time D2 has elapsed and a time t4 at which the predetermined time D1 has elapsed again.

Described specifically, the display unit 34 displays a coronal image 50 as shown in FIG. 5 before the execution of the navigator sequence NS. For instance, an operator sets an area for carrying out a navigator sequence onto the coronal image 50 displayed by the display unit 34 through the operation unit 32 as the navigator area NA. The set navigator area NA may overlap with the imaging area IA in which the imaging sequence IS is carried out. In the present embodiment as shown in FIG. 5, the navigator area NA is set as, for example, a rectangular area having long sides each parallel to the z-axis direction which intersects with the diaphragm 62 located between the lung 60 and the liver 61 and is approximately orthogonal to the diaphragm 62. Incidentally, any one of an axial section, a coronal section and a sagittal section may be used as the section of the subject 40.

At the navigator area NA, a first slice selection gradient magnetic field $G_s1$ is applied together with a high frequency pulse RF1 of a flip angle 90° as shown in FIG. 6 thereby to selectively 90°-excite a first slice surface containing the diaphragm 62 at the subject 40. Thereafter, a second slice selection gradient magnetic field $G_s2$ is applied to the subject 40 thereby to return the phase. Thereafter, a third slice selection gradient magnetic field $G_s3$ and a first phase encoding gradient magnetic field $G_\varphi1$ are applied together with a high frequency pulse RF2 of a flip angle 180° thereby to 180°-excite a second slice surface that intersects with the first slice surface in an area containing the diaphragm 62.

Then, first and second frequency encoding gradient magnetic fields Gf1 and Gf2 are applied such that frequency encoding is conducted, so that the scan section 2 acquires a magnetic resonance signal E generated from the area at which the first slice surface and the second slice surface intersect at the subject 40, as navigator data.

At the navigator area NA, a gradient magnetic field is applied so as to continuously vary in polarity in y and z directions alternately simultaneously with the transmission of each RF pulse, for example, as shown in Fig. 7 to select a slice of the subject 40 linearly. Then, such a cylindrical gradient echo-type navigator sequence that a read gradient magnetic field is applied in an x direction may be executed.

Here, as shown in FIG. 5 in the present embodiment, the navigator date needs position information in the direction (z-axis direction) approximately orthogonal to the diaphragm 62 and does not need position information in the direction (x-axis direction) approximately parallel to the diaphragm 62. Thus, the navigator sequence NS is a sequence for acquiring navigator data free of application of a phase encode gradient magnetic field for acquiring spatial information in the x-axis direction.

Next, as shown in FIG. 3, data processing on the navigator data obtained by the prescan is executed (ST20).

Here, one-dimensional Fourier transform is executed on the plural navigator data acquired by executing the navigator sequence NS at Step ST10. Thereafter, intensity and phase profiles on the plural navigator data subjected to the one-dimensional Fourier transform are generated. Each position of a body-moved region is detected in the intensity and phase profiles, thereby generating a position profile. Thus, a specific position of the region is detected in the position profile.

Figure 8:
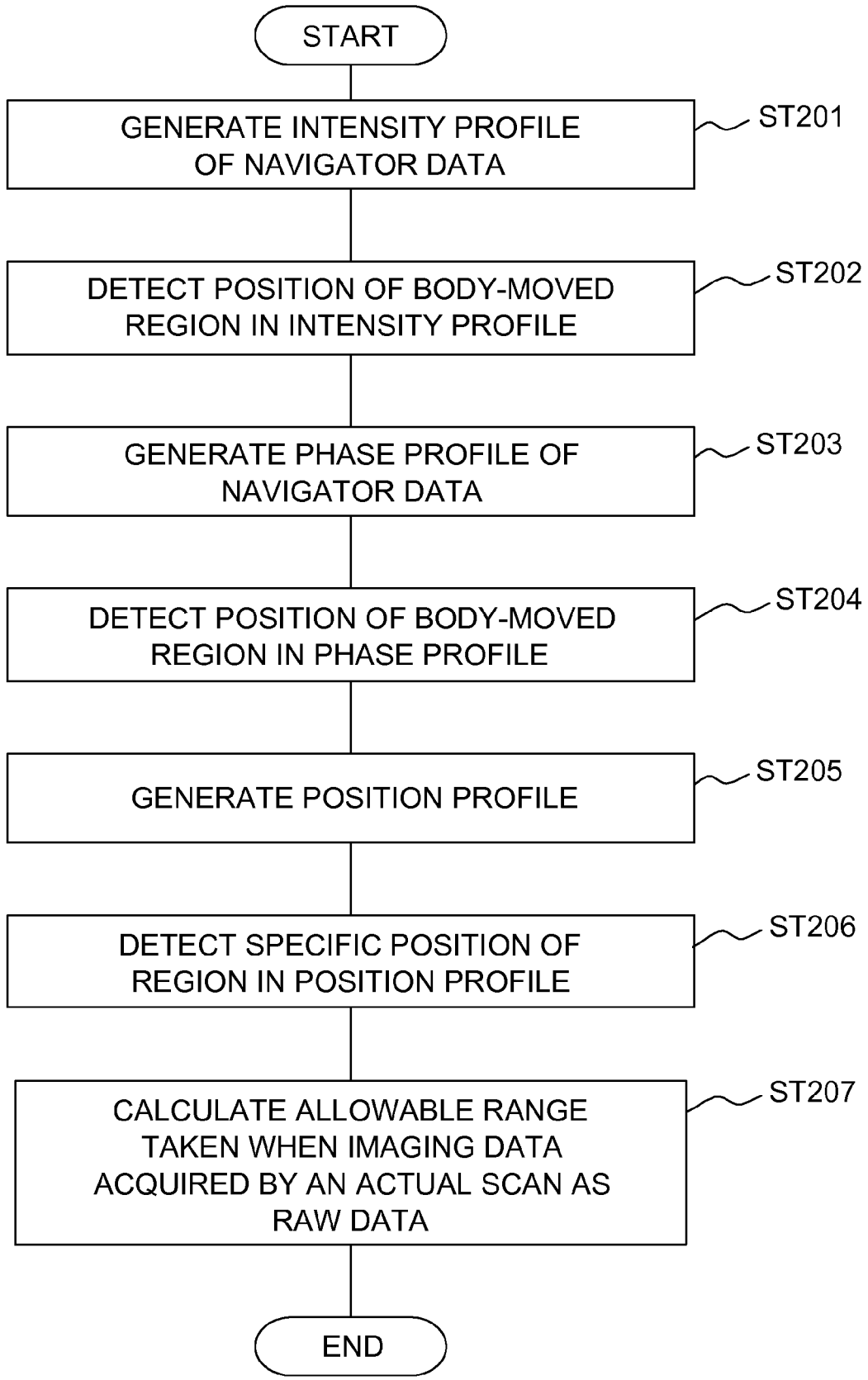
FIG. 8 is a flow chart showing the operation of detecting a specific position of a region of a subject from navigator data using the magnetic resonance imaging apparatus shown in FIG. 1.

FIG. 8 is a flow chart showing the operation of detecting a specific position of a region of a subject from navigator data in the one embodiment according to the invention.

An intensity profile of navigator data is generated as shown in FIG. 8 (ST201).

Figure 9A:
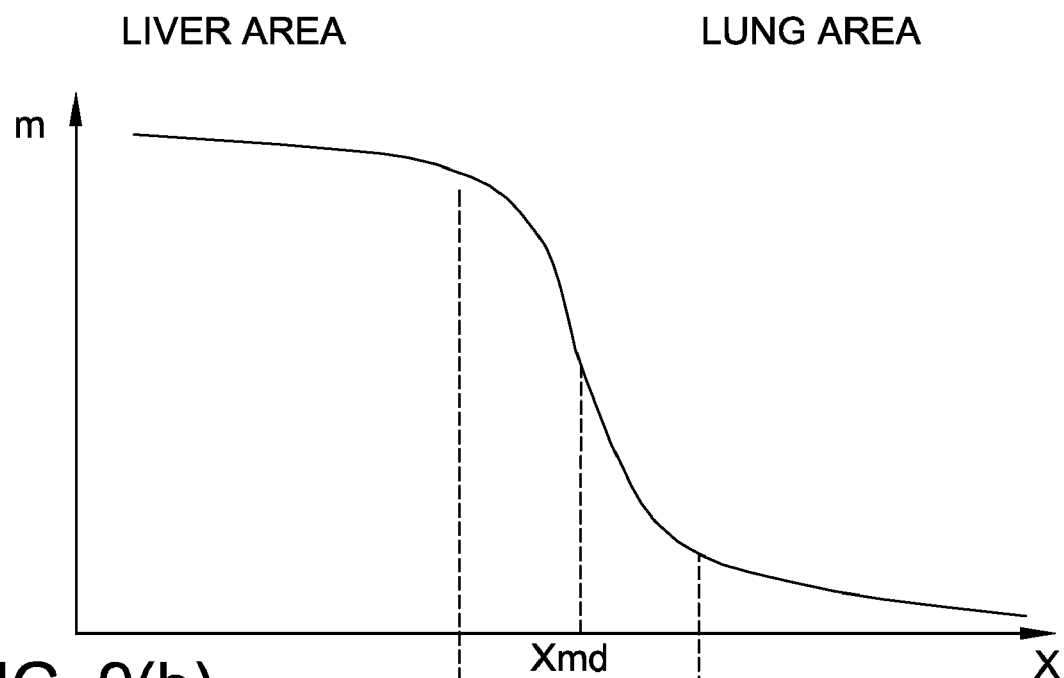
FIGS. 9($a$) and 9($b$) are diagrams showing an intensity profile and a phase profile obtained by one-dimensionally Fourier transforming navigator data in the one embodiment according to the invention.
Figure 9B:
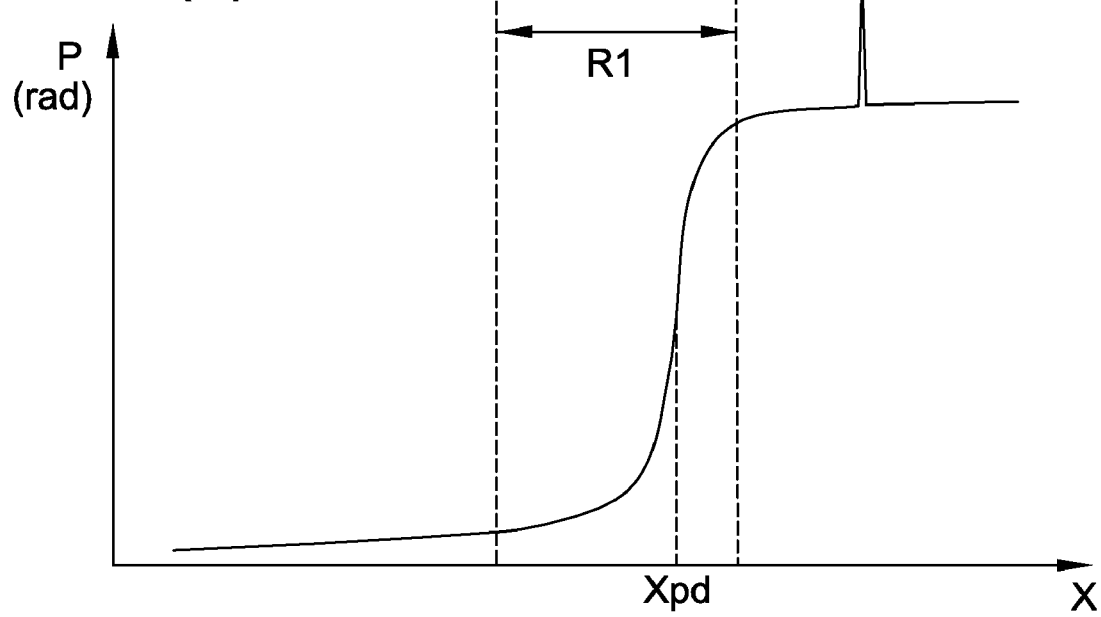

FIGS. 9(a) and 9(b) are diagrams showing an intensity profile and a phase profile obtained by one-dimensionally Fourier transforming navigator data in the one embodiment according to the invention. FIG. 9(a) shows an intensity profile obtained by plotting intensities, and FIG. 9(b) shows a phase profile obtained by plotting phases. Here, the horizontal axes shown in FIGS. 9(a) and 9(b) respectively indicate a position X. The position X corresponds to a position in a z-axis direction at the navigator area NA shown in FIG. 5. The vertical axis shown in FIG. 9(a) indicates signal intensity. FIG. 9(b) indicates the phase and the angle is expressed in radians. An area large in the value of an intensity m indicates the phase of the liver 61 shown in FIG. 5, and an area small in the value of the intensity m indicates the phase of the lung 60 shown in FIG. 5. An area large in the value of the phase P indicates the phase of the lung 60 shown in FIG. 5, and an area small in the value of the phase P indicates the phase of the liver 61 shown in FIG. 5. This is similar even in the drawings to be shown below. Incidentally, there is also a case in which the magnitudes of the phase values at the liver and lung are reversed each other.

Here, the intensity profile generation device 331 performs one-dimensional Fourier transform processing on the navigator data acquired at Step ST10 and thereby generates an intensity profile indicative of the relationship between the intensity m of navigator data and the position of the navigator area NA at the subject 40 as shown in FIG. 9(a).

Described specifically, the intensity profile generation device 331 executes one-dimensional Fourier transform processing on navigator data at a predetermined time D1, for example, and plots the relationship between the intensity m and position X of the navigator data assuming that the vertical axis is set as the intensity m of the navigator data, the horizontal axis is set as the position of the navigator area NA at the subject 40, and the end on the liver 61 side in the navigator area is set as the position X=0, thereby generating an intensity profile. Though the intensity profile may be displayed on the display unit 34, it may preferably be not displayed thereon.

Next, as shown in FIG. 8, the position of each body-moved region is detected in the intensity profile (ST202).

Here, the position detection device 333 detects the position of each body-moved region at the subject 40 in the intensity profile generated at Step ST201.

Described specifically, when, for example, the diaphragm 62 lying in the boundary between the liver 61 and the lung 60 is taken as the body-moved region of the subject 40, the position detection device 333 detects the position Xmd of the diaphragm 62 in the intensity profile. The position Xmd of the diaphragm 62 in the intensity profile is detected by the differential method or Du method, for example, as a method for detecting the position of the diaphragm 62. The position Xmd of the diaphragm 62 in the intensity profile is shown in FIGS. 9(a) and 9(b).

Next, as shown in FIG. 8, a phase profile of navigator data is generated (ST203).

Here, the phase profile generation device 332 performs one-dimensional Fourier transform processing on the navigator data acquired at Step ST10 and thereby generates a phase profile indicative of the relationship between the phase P of navigator data and the position of the navigator area NA at the subject 40 as shown in FIG. 9(b).

Described specifically, the phase profile generation device 332 executes one-dimensional Fourier transform processing on navigator data at a predetermined time D1, for example, and plots the relationship between the phase P and position Xp of the navigator data assuming that the vertical axis is set as the phase P of the navigator data, the horizontal axis is set as the position of the navigator area NA at the subject 40, and the end on the liver 61 side in the navigator area is set as the position Xp=0, thereby generating a phase profile. Though the phase profile may be displayed on the display unit 34, it may preferably be not displayed thereon.

Next, as shown in FIG. 8, the position of each body-moved region is detected in the phase profile (ST204).

Here, the position detection device 333 detects the position of each body-moved region at the subject 40 in the phase profile generated at Step ST203.

Described specifically, when, for example, the diaphragm 62 lying in the boundary between the liver 61 and the lung 60 is taken as the body-moved region of the subject 40, the position detection device 333 detects the position Xpd of the diaphragm 62 in the phase profile. The position Xpd of the diaphragm 62 in the phase profile is detected by the differential method or Du method, for example, as a method for detecting the position of the diaphragm 62. Here, as the range for detecting the position Xpd of the diaphragm 62 in the phase profile by the differential method or Du method, as shown in FIG. 9, a reference range R1 is set with the Xmd of the diaphragm 62 in the intensity profile, which has been detected at Step ST202, as the reference. The position Xpd of the diaphragm 62 is detected by the differential method or Du method in the phase profile lying within the reference range R1. For example, the reference range R1 to be detected is set between lines of ±10 pixels in an x-axis direction of FIG. 9 with the position Xmd of the diaphragm 62 in the intensity profile as the center. The positions Xmd and Xpd of the diaphragm 62 in the intensity and phase profiles calculated from the navigator data acquired at the same time are close to each other. The position Xpd of the diaphragm 62 in the phase profile is determined on the basis of the position Xmd of the diaphragm 62 in the intensity profile.

This results in the case in which as shown in FIG. 9(b), a peak occurs in a position other than the position of the diaphragm 62 due to the influence of the blood or the like in the phase profile, and this peak is misrecognized as the position Xpd of the diaphragm 62 in the phase profile. Thus, this misrecognition can be prevented by determining the position Xpd of the diaphragm 62 in the phase profile, based on the position Xmd of the diaphragm 62 in the intensity profile.

Next, as shown in FIG. 8, a position profile is generated (ST205).

Figure 10:
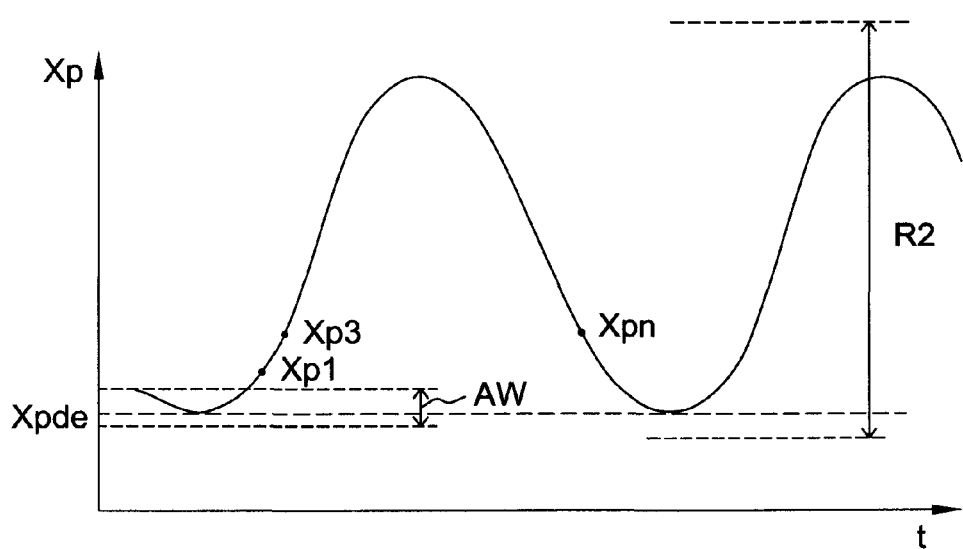
FIG. 10 is a diagram showing a position profile indicative of the relationship between the position of a region in a navigator area of the subject and time.

FIG. 10 is a diagram showing a position profile indicative of the relationship between the position of a region in a navigator area of a subject and time in the one embodiment according to the invention.

Here, the position profile generation device 334 generates a position profile on the basis of a plurality of positions Xpd of the diaphragm 62 in the phase profile, which have been detected by repeatedly executing Steps ST201 through ST204.

Described specifically, the position profile generation device 334 generates a position profile obtained by plotting, as shown in FIG. 10, a position Xp1 of the body-moved region of the subject 40 in the phase profile detected by executing the above Steps ST201 through ST204 on the navigator data acquired by the prescan executed by the scan section 2 during a predetermined time D1, a position Xp3 of the body-moved region of the subject 40 in the phase profile detected by executing the above Steps ST201 through ST204 on the navigator data acquired by the prescan executed by the scan section 2 during a predetermined time D3, and a position Xpn of the body-moved region of the subject 40 in the phase profile detected by executing the above Steps ST201 through ST204 on the navigator data acquired by the prescan executed by the scan section 2 during a predetermined time Dn, respectively, with the vertical axis as the position Xp of the region and the horizontal axis as the acquired time of navigator data. The position profile may preferably be displayed on the display unit 34.

Next, as shown in FIG. 8, a region located in a specific position in the position profile is detected (ST206).

Figure 11:
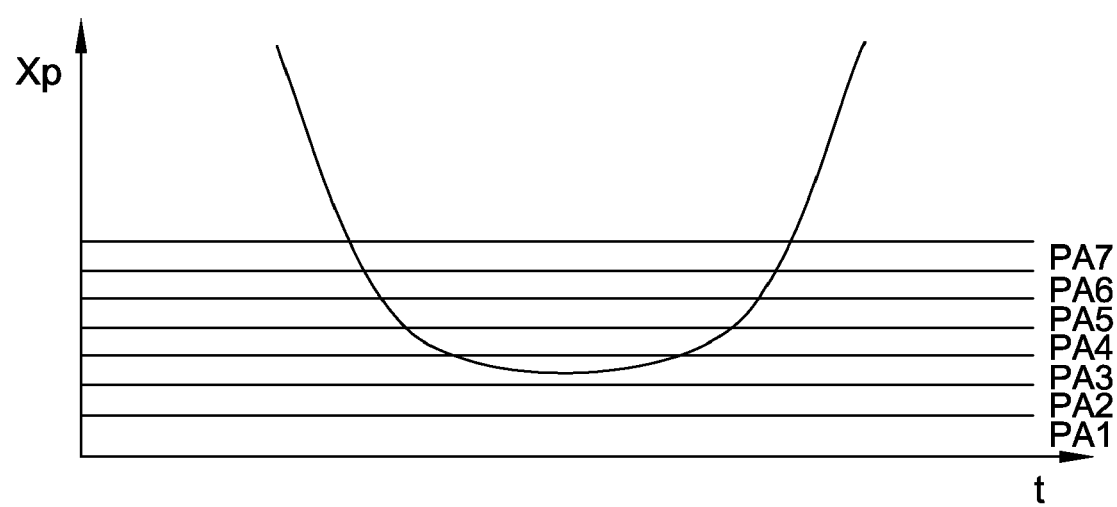
FIG. 11 is an enlarged diagram of the position profile shown in FIG. 10.

FIG. 11 is an enlarged view of the position profile shown in FIG. 10.

The specific position detection device 335 detects a region located in a specific position at the subject 40 in the position profile generated at Step ST205 herein. Here, the specific position at the subject 40 corresponds to the position of a region of the subject 40 at the time that it is desired to generate a slice image in an imaging area IA.

Described specifically, when, for example, the region of the subject 40 is of the diaphragm, the specific position of the diaphragm 62 at the subject 40 corresponds to a position of the diaphragm 62 at time that the subject 40 is brought to the completion of expiration thereof. The specific position detection device 335 detects a position Xpde of the diaphragm 62 in the position profile at the time that the subject 40 is brought to the completion of expiration thereof.

A method for detecting the position Xpde of the diaphragm 62 at the time that the expiration of the subject 40 has been completed, is as follows. As shown in FIG. 11, for example, the position in the position profile is divided in predetermined width, and the area largest in the number of data at the corresponding position, of the so-divided respective areas is detected as the position of the diaphragm 62 at the time that the expiration thereof has been ended. Since the number of data at the position lying within the divided area PA3 of the divided areas PA1 through PA7 is largest in FIG. 11, for example, the divided area PA3 is detected as the position of the diaphragm 62 at the time that the expiration has been completed.

The minimum value of the position of the diaphragm 62 is detected and the position may be set as the position Xpde of the diaphragm 62 at the time that the expiration has been completed.

Next, as shown in FIG. 8, an allowable range taken when the imaging data acquired by the actual scan is acquired as raw data is calculated (ST207).

Here, an allowable range AW set as the reference taken when the raw data acquisition device 336 acquires the imaging data acquired by the actual scan as raw data, is calculated based on the specific position detected at Step ST206.

Described specifically, the width of ±2 mm from the specific position of the region at the subject 40, which has been detected at Step S206, for example, is calculated as the allowable range AW as shown in FIG. 10.

When the region is of the diaphragm 62, for example, the lines (4 mm in total) of 2 mm extended to the liver 61 and lung 60 sides as viewed from the position Xpde of the diaphragm 62 at the completion of the expiration, which has been detected as the specific position of the region at Step ST206, are calculated as the allowable range AW.

Next, as shown in FIG. 3, the actual scan is executed (ST30).

Here, the scan section 2 executes a navigator sequence NS at a navigator area NA for the subject 40 and executes an imaging sequence IS at an imaging area IA alternately with respect to it.

Described specifically, for example, the scan section 2 executes the navigator sequence NS as the actual scan as shown in FIG. 4 between a time t11 at which the navigator sequence NS is started and a time t12 at which a predetermined time D11 has elapsed. Then, the scan section 2 executes the imaging sequence IS between a time t13 at which a predetermined time D12 has elapsed and a time t14 at which a predetermined time D13 has elapsed.

The imaging sequence IS is first executed and thereafter the navigator sequence NS may be conducted.

In the navigator sequence NS, a first slice selection gradient magnetic field $G_s1$ is applied together with a high frequency pulse RF1 of a flip angle 90° as shown in FIG. 6 at the same navigator area NA as the navigator area NA at the prescan thereby to selectively 90°-excite a first slice surface containing the diaphragm 62 at the subject 40. Thereafter, a second slice selection gradient magnetic field $G_s2$ is applied to the subject 40 thereby to return the phase. Thereafter, a third slice selection gradient magnetic field $G_s3$ and a first phase encoding gradient magnetic field $G_\phi1$ are applied together with a high frequency pulse RF2 of a flip angle 180° thereby to 180°-excite a second slice surface that intersects with the first slice surface in an area containing the diaphragm 62.

Then, first and second frequency encoding gradient magnetic fields $G_f1$ and $G_f2$ are applied such that frequency encoding is conducted, so that the scan section 2 acquires a magnetic resonance signal E generated from the area at which the first slice surface and the second slice surface intersect at the subject 40, as navigator data.

At the navigator area NA, a gradient magnetic field is applied so as to continuously vary in polarity in y and z directions alternately simultaneously with the transmission of each RF pulse, for example, as shown in FIG. 7 to select a slice of the subject 40 linearly. Then, such a cylindrical gradient echo-type navigator sequence that a read gradient magnetic field is applied in an x direction may be executed.

Here, as shown in FIG. 5 in the present embodiment, the navigator date needs position information in the direction (z-axis direction) approximately orthogonal to the diaphragm 62 and does not need position information in the direction (x-axis direction) approximately parallel to the diaphragm 62. Thus, the navigator sequence NS is a sequence for acquiring navigator data free of application of a phase encode gradient magnetic field for acquiring spatial information in the x-axis direction.

The imaging sequence IS can make use of a pulse sequence such as a spin echo (SE) method, a gradient echo (GE) method or the like.

Next, as shown in FIG. 3, the processing of data obtained by the actual scan is executed (ST40).

Here, one-dimensional Fourier transform is executed on the plural navigator data acquired by executing the navigator sequence NS at Step ST30. Thereafter, phase profiles on the plural navigator data subjected to the one-dimensional Fourier transform are generated. Each position of a body-moved region is detected in each of the phase profiles, thereby generating a position profile. Thus, imaging data is acquired as raw data, based on the position file.

Figure 12:
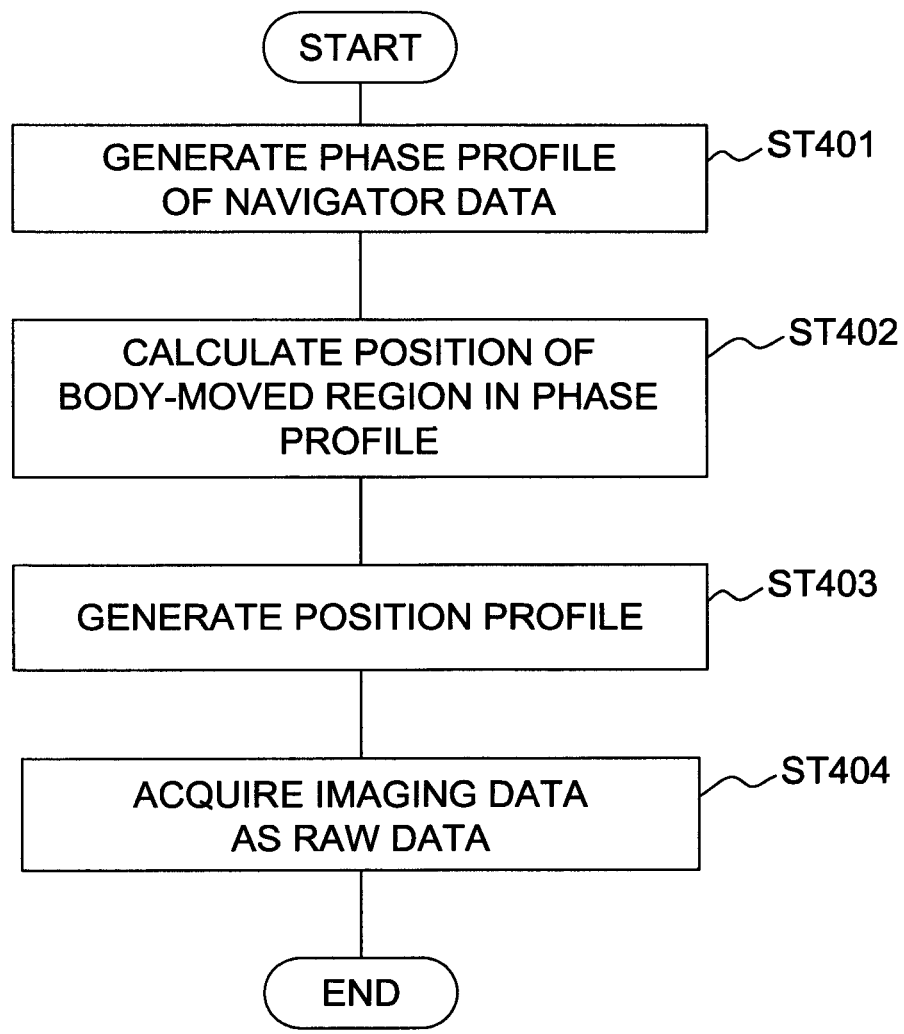
FIG. 12 is a flow chart showing the operation of acquiring imaging data of the subject as raw data from data obtained by an actual scan by the magnetic resonance imaging apparatus shown in FIG. 1.
Figure 13:
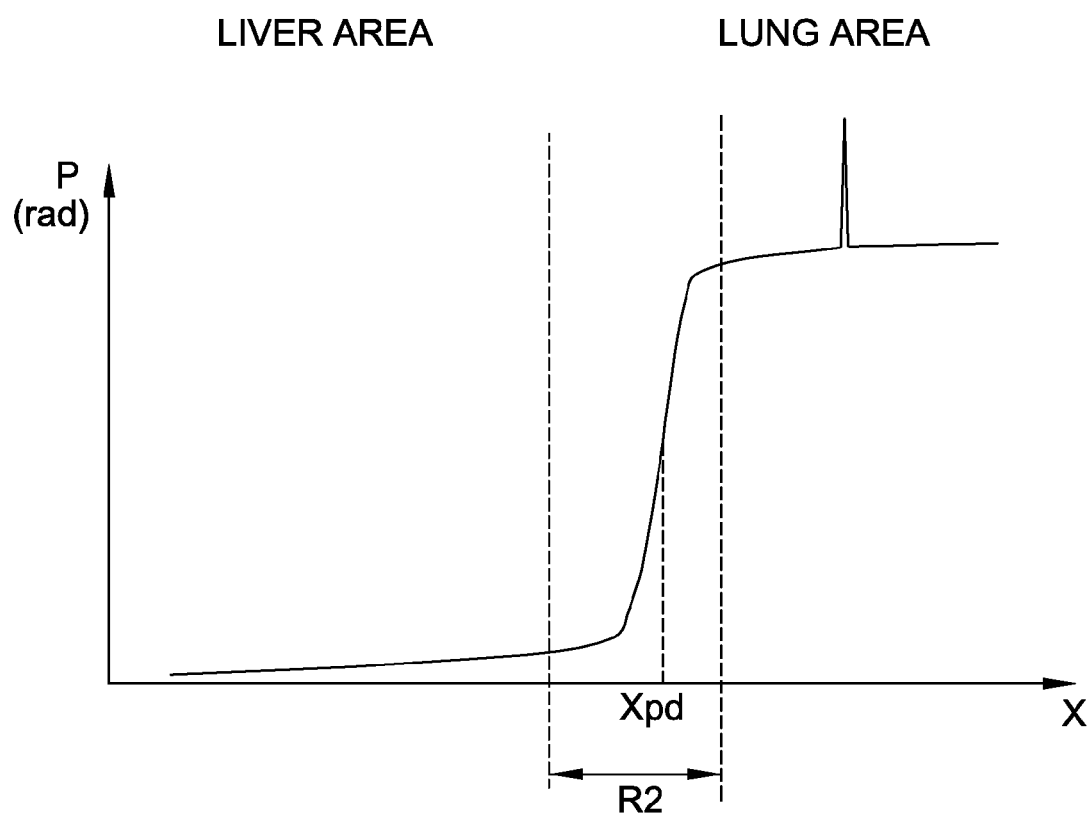
FIG. 13 is a diagram showing a phase profile obtained by one-dimensionally Fourier transforming navigator data.

FIG. 12 is a flow chart showing the operation of acquiring imaging data of the subject as raw data from the data obtained by the actual scan in the one embodiment according to the invention. FIG. 13 is a diagram showing a phase profile obtained by one-dimensionally Fourier transforming navigator data in the one embodiment according to the invention. The horizontal axis indicates the position and the vertical axis indicates the phase. The angle is expressed in radians.

As shown in FIG. 12, a phase profile about navigator data is first generated (ST401).

Here, the phase profile generation device 332 performs one-dimensional Fourier transform processing on the navigator data acquired at Step ST30 and thereby generates a phase profile indicative of the relationship between the phase P of navigator data and the position X of a navigator area NA at the subject 40 as shown in FIG. 13.

Described specifically, the phase profile generation device 332 executes one-dimensional Fourier transform processing on navigator data at a predetermined time D1, and plots the relationship between the phase P and position Xp of the navigator data assuming that the vertical axis is set as the phase P of the navigator data, the horizontal axis is set as the position of the navigator area NA at the subject 40, and the end on the liver 61 side in the navigator area is set as the position Xp=0, thereby generating a phase profile. Though the phase profile may be displayed on the display unit 34, it may preferably be not displayed thereon.

Next, as shown in FIG. 12, the position of each body-moved region is detected in the phase profile (ST402).

Here, the position profile generation device 334 detects the position of each body-moved region at the subject 40 in the phase profile generated at Step ST401.

Described specifically, when, for example, the diaphragm 62 lying in the boundary between the liver 61 and the lung 60 is taken as the body-moved region of the subject 40, the position profile generation device 334 detects a position Xpd11 of the diaphragm 62 in the phase profile. The position Xpd11 of the diaphragm 62 in the phase profile is detected by the differential method or Du method, for example, as a method for detecting the position of the diaphragm 62.

Here, as the range for detecting the position Xpd11 of the diaphragm 62 in the phase profile by the differential method or Du method, as shown in FIG. 10, a reference range R2 is set with a position Xpde11 of the diaphragm 62 at the completion of expiration, which has been detected at Step ST206, as the reference. The position Xpd of the diaphragm 62 lying within the reference range R2 is detected by the differential method or Du method in the phase profile shown in FIG. 13. For example, the lines which are extended by 10 pixels to the lung 60 side as viewed from the position Xpde of the diaphragm 62 at the completion of expiration, corresponding to the specific position detected by the specific position detection device 335 and which are extended by 40 pixels to the liver 61 side as viewed therefrom are set as the reference range R2 to be detected.

Next, as shown in FIG. 12, a position profile is generated (ST403).

Figure 14:
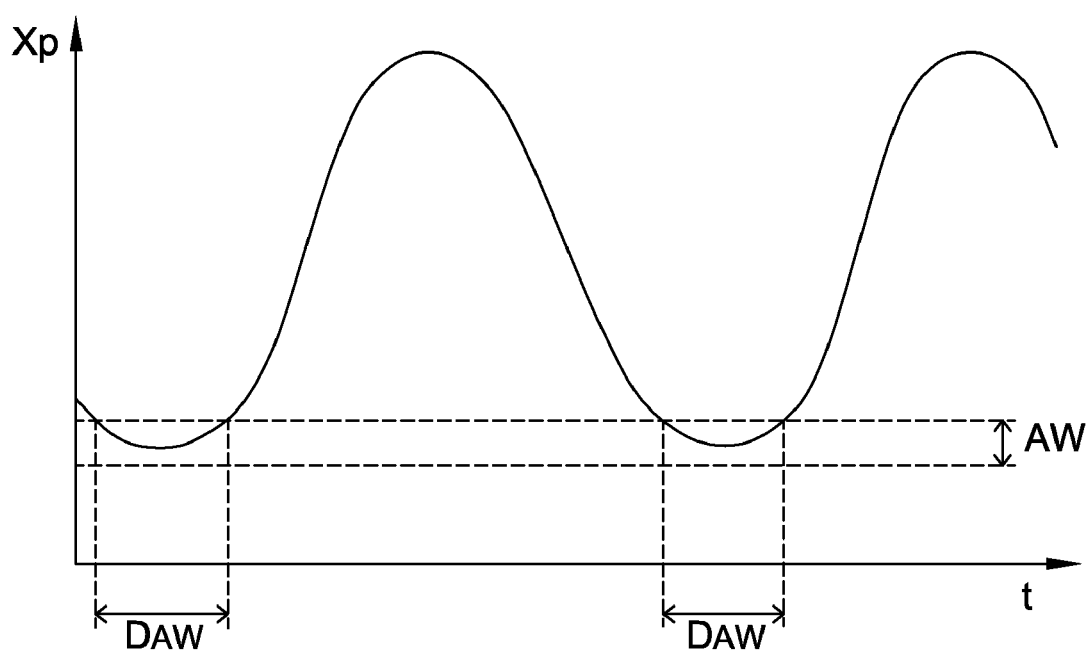
FIG. 14 is a diagram illustrating a position profile indicative of the relationship between the position of a region in a navigator area of the subject and time.
Figure 15:
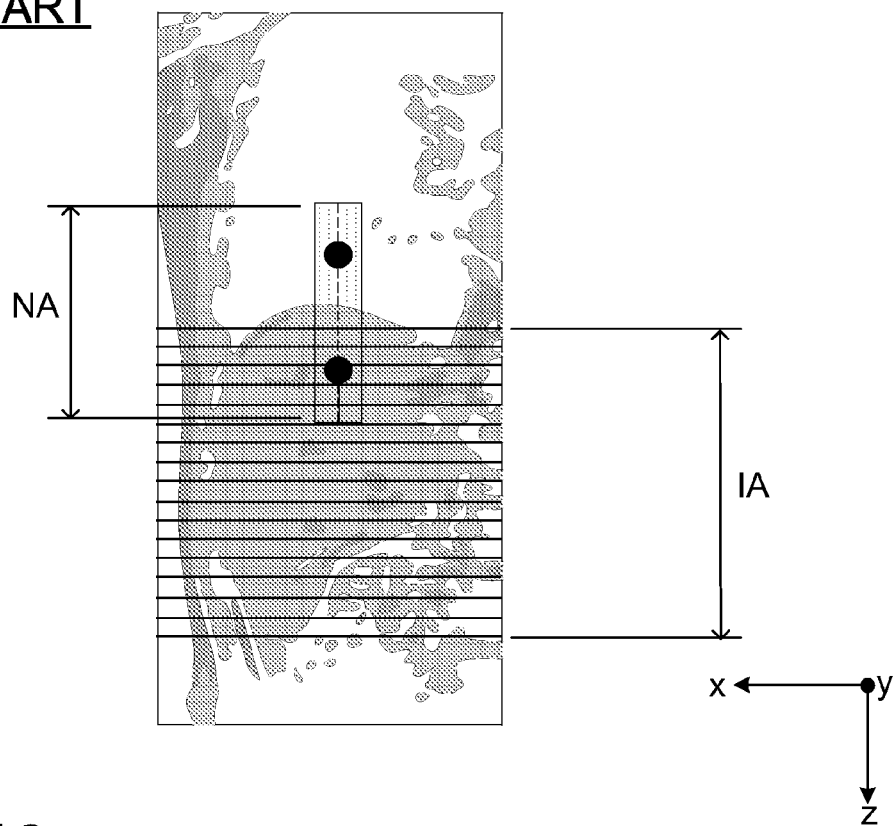
FIG. 15 is a diagram showing a coronal image indicating a navigator area NA and an imaging area IA for describing a related art.
Figure 16:
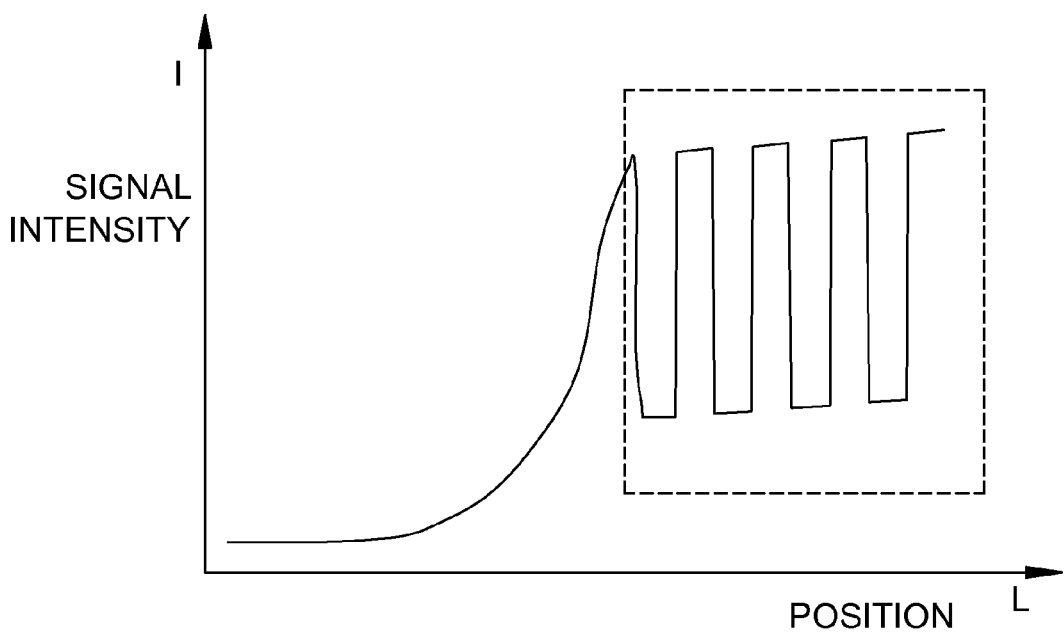
FIG. 16 is a diagram illustrating a signal intensity profile for describing the related art.

FIG. 14 is a diagram showing a position profile indicative of the relationship between the position of a region in a navigator area of a subject and time in the one embodiment according to the invention.

Here, the position profile generation device 334 generates a position profile on the basis of a plurality of positions Xpd11 of the diaphragm 62 in the phase profile, which have been detected by repeatedly executing Steps ST401 and ST402.

Described specifically, the position profile generation device 334 generates a position profile obtained by plotting, as shown in FIG. 14, a position Xp11 of the body-moved region of the subject 40 in the phase profile detected by executing the above Steps ST401 and ST402 on the navigator data acquired by the actual scan executed by the scan section 2 during a predetermined time D11, a position Xp15 of the body-moved region of the subject 40 in the phase profile detected by executing the above Steps ST401 and ST402 on the navigator data acquired by the prescan executed by the scan section 2 during a predetermined time D15, and a position Xpn of the body-moved region of the subject 40 in the phase profile detected by executing the above Steps ST401 and ST402 on the navigator data acquired by the prescan executed by the scan section 2 during a predetermined time Dn, respectively, with the vertical axis as the position Xp of the region and the horizontal axis as the acquired time of navigator data. The position profile may preferably be displayed on the display unit 34.

Next, as shown in FIG. 12, imaging data is acquired as raw data (ST404).

Here, the raw data acquisition device 336 determines whether the position profile generated at Step ST403 falls within the allowable range AW calculated at Step ST207, and acquires imaging data corresponding to navigator data set as the origin of the position profile lying within the allowable range AW.

Described specifically, as shown in FIG. 14, it is determined whether the position profile generated at Step ST403 falls within the allowable range AW calculated at Step ST207. Imaging data acquired by an imaging sequence IS executed during each time DAW of the position profile lying within the allowable range AW is acquired as raw data.

Next, a slice image is generated as shown in FIG. 3 (ST50).

Here, the image generation device 337 generates a slice image of the subject 40 using the imaging data acquired at Step ST404. For example, the image generation device 337 generates a slice image of the liver 61 at the subject 40. Then, the image generation device 337 outputs the generated slice image to the display unit 34.

In the one embodiment of the invention as described above, the navigator area NA is set and the navigator sequence NS is executed as the prescan in the set navigator area NA. One-dimensional Fourier transform is performed on the acquired navigator data and thereby each intensity profile obtained by plotting the intensity of the navigator data and each phase profile obtained by plotting the phase thereof are generated. The position of each body-moved region is detected in the intensity profile, and the position of the body-moved region is detected in the phase profile, based on the detected position. The position profile indicative of the relationship between the position of each region and time is generated based on the position of the body-moved region in each phase profile detected every time. Then, the position of each body-moved region lying in the specific position is detected in the position profile. Next, each of the navigator sequence NS and the imaging sequence IS is executed as the actual scan. One-dimensional Fourier transform is executed on the acquired navigator data and thereby the phase profile obtained by plotting the phase of the navigator data is generated. The position of each body-moved region is detected in the phase profile on the basis of the position of the body-moved region located in the specific position, which has been detected based on the navigator data obtained by the prescan. Then, the position profile indicative of the relationship between the position of each region and the time is generated based on the position of the body-moved region in the phase profile detected every time. The imaging data is acquired as the raw data, based on the position profile and the detected specific position. The slice image is generated based on the acquired raw data.

Calculating the specific position of each region at the subject using the intensity and phase profiles obtained by executing one-dimensional Fourier transform processing on the navigator data obtained by executing the navigator sequence NS in this way makes it possible to calculate the specific position accurately. Therefore, since the position of the region can be detected accurately, it is possible to prevent the occurrence of body-motion artifacts in the generated slice image and obtain the slice image good in image quality.

Incidentally, the invention is not limited to the above embodiment upon its implementation. Various modified forms can be adopted.

In the embodiment of the invention, as the method for acquiring the imaging data as the raw data, the navigator sequence NS and the imaging sequence IS are executed upon the actual scan thereby to acquire the navigator data and the imaging data. Thereafter, the raw data acquisition device 336 acquires the raw data from the imaging data, based on the result of the data processing on the navigator data. The invention is not limited to it. For example, the controller 30 may determine, based on the result of the data processing on the navigator data whether the scan section 2 carries out the imaging sequence IS. By determining based on the result of the data processing on the navigator data whether the imaging sequence IS is executed, imaging can be started with the timing desirable for the subject 40.

Although in the embodiment of the invention, the navigator sequence NS at the actual scan is executed and thereafter the imaging sequence IS is executed, the invention is not limited to it. Upon the actual scan, the imaging sequence IS is executed and thereafter the navigator sequence NS may be carried out.

Although in the embodiment of the invention, the navigator sequence NS at the prescan is performed, the data processing is performed on the navigator data acquired by executing the navigator sequence NS at the prescan, thereafter the navigator sequence NS and the imaging sequence IS at the prescan are executed, and thereafter the data processing is performed on the navigator data acquired by executing the navigator sequence NS at the actual scan, the invention is not limited to it. The data processing is performed on the navigator data acquired by executing the navigator sequence NS at the prescan after execution of the navigator sequence NS at the prescan. The data processing is executed on the navigator data acquired by executing the navigator sequence NS at the actual scan after execution of the navigator sequence NS and the imaging sequence IS at the actual scan. Then, the data processing may be performed on the navigator data acquired by executing the navigator sequence NS at the actual scan after execution of the data processing on the navigator data acquired by executing the navigator sequence NS at the prescan. Thus, for example, data processing is performed on navigator data acquired by executing the navigator sequence NS at the prescan, thereafter executing the navigator sequence NS and the imaging sequence IS at the actual scan and executing the navigator sequence NS at the prescan after that. Thereafter, data processing may be performed on navigator data acquired by executing the navigator sequence NS at the actual scan.

Although in the embodiment of the invention, the range lying between the lines of ±10 pixels from the position Xmd of the diaphragm 62 in the intensity profile is set as the reference range R1 to be detected, the range lying between the lines extended by 10 pixels to the lung 60 side from the position Xpde of the diaphragm 62 at the completion of expiration, corresponding to the specific position detected by the specific position detection device 335 and extended by 40 pixels to the liver 61 side is set as the reference range R2 to be detected, and ±2 mm as viewed from the position of the diaphragm 62 of Xpde with respect to the detected respiration is set as the allowable range AW, the invention is not limited to it.

Any one of an axial section, a coronal section and a sagittal section may be used as the section of the subject 40.

Incidentally, the intensity profile generation device 331 employed in the present embodiment corresponds to an intensity profile generation device of the invention. The phase profile generation device 332 employed in the present embodiment corresponds to a first phase profile generation device or a second phase profile generation device of the invention. The position detection device 333 employed in the present embodiment corresponds to a first position detection device, a second position detection device, a first reference range set device or a second reference range set device of the invention. The position profile generation device 334 employed in the present embodiment corresponds to a first position profile generation device or a second position profile generation device of the invention.

Many widely different embodiments of the invention may be configured without departing from the spirit and the scope of the present invention. It should be understood that the present invention is not limited to the specific embodiments described in the specification, except as defined in the appended claims.

What is claimed is:

1. A magnetic resonance imaging apparatus configured to acquire magnetic resonance signals from a navigator area containing a plurality of body-moved regions of a subject as first navigator data by repeatedly executing a first navigator sequence, to acquire magnetic resonance signals from the navigator area as second navigator data by repeatedly executing a second navigator sequence, to acquire magnetic resonance signals from an imaging area of the subject as imaging data using an imaging sequence, the imaging data based on positions of the plurality of regions obtained from the second navigator data, the positions based on the first navigator data, and to generate an image, based on raw data, said magnetic resonance imaging apparatus comprising:

a first navigator data processor configured to:

generate a phase profile for each of the first navigator data as a first phase profile with respect to each of the first navigator data, wherein the first phase profile plots a phase component of the first navigator data versus a position of the first navigator data in the navigator area;

detect a position of each region with respect to each first phase profile based on a position of each region in an intensity profile;

generate a position profile plotting a plurality of region positions versus each time at which the first navigator sequence is repeatedly executed; and detect a specific position in the position profile;

a second navigator data processor configured to:

generate a phase profile for each of the second navigator data as a second phase profile with respect to each of the second navigator data;

detect the position of each region with respect to each second phase profile within a reference range set so as to contain the specific position, based on each second phase profile; and acquire the position of each region with respect to each second phase profile as its corresponding position data; and a raw data acquiring unit configured to acquire imaging data as raw data, the imaging data obtained by the imaging sequence corresponding to the second navigator sequence, based on the position data in the second phase profile.

2. The magnetic resonance imaging apparatus according to claim 1, wherein said first navigator data processor comprises:

an intensity profile generation device configured to generate the intensity profile plotting the intensity of each of the first navigator data versus each position in the navigator area with respect to each of the first navigator data;

a first position detection device configured to detect the position of each region with respect to each intensity profile and acquiring the position of each region with respect to each intensity profile as its corresponding first position data;

a first reference range set device configured to set a first reference range with respect to each intensity profile such that the first reference range contains data corresponding to the first position data;

a first phase profile generation device configured to generate the first phase profile;

a second position detection device configured to detect the position of each region within each first reference range with respect to each first phase profile and acquiring the position of each region within each first reference range as its corresponding second position data;

a first position profile generation device configured to generate a first position profile plotting respective positions corresponding to respective second position data versus each time at which the first navigator sequence is repeatedly executed; and a specific position detection device configured to detect a specific position in the first position profile, and wherein said second navigator data processor comprises:

a second phase profile generation device configured to generate a second phase profile plotting a phase of each second navigator data versus each position in the navigator area with respect to each second navigator data;

a second reference range set device configured to set a second reference range such that the second reference range contains the specific position at each region, which has been detected by said specific position detection device;

a third position detection device configured to detect the position of each region with respect to each second phase profile within the second reference range and acquiring the position of each region with respect to each second phase profile as its corresponding third position data; and a second position profile generation device configured to generate a second position profile plotting the positions corresponding to the respective third position data versus each time at which the second navigator sequence is repeatedly executed.

3. The magnetic resonance imaging apparatus according to claim 2, wherein said raw data acquisition device is configured to select raw data from the imaging data, the imaging data acquired during the time corresponding to the second position data lying within a third reference range set so as to contain the specific position of each region.

4. The magnetic resonance imaging apparatus according to claim 3, wherein when the second position data falls within the third reference range set so as to contain the specific position of each region, an imaging sequence is executed to acquire imaging data.

5. The magnetic resonance imaging apparatus according to claim 2, wherein said specific position detection device is configured to detect an area largest in the number of position data, which is contained in respective areas obtained by dividing the position in the first position profile in predetermined width, as the specific position of each region.

6. The magnetic resonance imaging apparatus according to claim 2, wherein said specific position detection device is configured to detect a minimum value of the position data in the first position profile as the specific position of each region.

7. The magnetic resonance imaging apparatus according to claim 2, wherein each of the first navigator data and the second navigator data is obtained from a diaphragm as the region.

8. The magnetic resonance imaging apparatus according to claim 2, wherein said intensity profile generation device is configured to one-dimensionally Fourier transform the first navigator data to generate the intensity profile, wherein said first phase profile generation device is configured to one-dimensionally Fourier transform the first navigator data to generate the first phase profile, and wherein said second phase profile generation device is configured to one-dimensionally Fourier transform the second navigator data to generate the second phase profile.

9. The magnetic resonance imaging apparatus according to claim 2, wherein said first position detection device is configured to obtain the first position data by a differential method.

10. The magnetic resonance imaging apparatus according to claim 2, wherein said second position detection device is configured to obtain the second position data by the differential method.

11. An image generating method comprising:

repeatedly executing a first navigator sequence for acquiring magnetic resonance signals from a navigator area containing body-moved regions of a subject as first navigator data;

repeatedly executing a second navigator sequence for acquiring magnetic resonance signals from the navigator area as second navigator data;

executing an imaging sequence for acquiring magnetic resonance signals from an imaging area of the subject as imaging data, based on positions of the regions obtained from the second navigator data, based on the first navigator data, thereby acquiring the imaging data as raw data;

generating a phase profile for each of the first navigator data as a first phase profile with respect to each of the first navigator data, wherein the first phase profile plots a phase component of the first navigator data versus a position of the first navigator data in the navigator area;

detecting a position of each region with respect to each first phase profile based on a position of each region in an intensity profile;

generating a position profile plotting a plurality of region positions versus each time at which the first navigator sequence is repeatedly executed;

detecting a specific position in the position profile;

generating a phase profile for each of the second navigator data as a second phase profile with respect to each of the second navigator data;

detecting the position of each region with respect to each second phase profile within a reference range set so as to contain the specific position, based on each second phase profile, and acquiring the position of each region with respect to each second phase profile as its corresponding position data; and acquiring the imaging data as raw data, based on the position data in the second phase profile.

12. The image generating method according to claim 11, further comprising:

generating the intensity profile plotting the intensity of each of the first navigator data versus each position in the navigator area;

detecting the position of each region with respect to the intensity profile and acquiring the position of each region with respect to the intensity profile as first position data;

setting a first reference range with respect to the intensity profile such that the first reference range contains data corresponding to the first position data;

detecting the position of each region within the first reference range set with respect to the first phase profile and acquiring the position of each region within the first reference range as second position data;

generating a first position profile plotting a plurality of second position data versus time at which the first navigator sequence is repeatedly executed; and detecting a specific position in the first position profile;

generating a second phase profile plotting a phase of the second navigator data versus each position in the navigator area;

setting a second reference range such that the second reference range contains the specific position at each region;

detecting the position of each region with respect to the second phase profile within the second reference range and acquiring the position of each region with respect to the second phase profile as third position data; and generating a second position profile plotting a plurality of the third position data versus each time at which the second navigator sequence is repeatedly executed.

13. The image generating method according to claim 12, wherein acquiring the imaging data comprises:

setting a third reference range from the imaging data such that the third reference range contains the specific position of each region; and selecting, as raw data, imaging data acquired during the time corresponding to the second position data lying within the third reference range.

14. The image generating method according to claim 13, wherein acquiring imaging data further comprises setting the third reference range from the imaging data such that the third reference range contains the specific position of each region, and wherein when the second position data falls within the third reference range, the imaging sequence is executed to acquire imaging data.

15. The image generating method according to claim 12, wherein an area largest in the number of data at each position in the first position profile, which is contained in respective areas obtained by dividing the position in the first position profile in predetermined width, is detected as the specific position of each region.

16. The image generating method according to claim 12, wherein a minimum value of each position in the first position profile is detected as the specific position of each region.

17. The image generating method according to claim 12, wherein each of the first navigator data and the second navigator data is obtained from a diaphragm as the region.

18. The image generating method according to claim 12, wherein the second navigator data is one-dimensionally Fourier transformed thereby to generate the intensity profile, wherein the first navigator data is one-dimensionally Fourier transformed thereby to generate the first phase profile, and wherein the second navigator data is one-dimensionally Fourier transformed thereby to generate the second phase profile.

19. The image generating method according to claim 12, wherein the first position data is detected by a differential method.

20. The image generating method according to claim 12, wherein the second position data is detected by the differential method.

* * * * *